United States Patent [19]
Miller et al.

[11] Patent Number: 6,060,247
[45] Date of Patent: May 9, 2000

[54] POST-MITOTIC NEURONS CONTAINING ADENOVIRUS VECTORS THAT MODULATE APOPTOSIS AND GROWTH

[75] Inventors: Freda D. Miller, Montreal; Ruth S. Slack, Napean, both of Canada

[73] Assignee: McGill University, West Montreal, Canada

[21] Appl. No.: 08/995,050

[22] Filed: Nov. 18, 1997

Related U.S. Application Data

[60] Provisional application No. 60/031,057, Nov. 18, 1996.

[51] Int. Cl.[7] ............................................ C12Q 1/68
[52] U.S. Cl. .............................. 435/6; 435/456; 435/377
[58] Field of Search ..................................... 435/456, 457, 435/368, 375, 377, 6, 320.1, 235.1

[56] References Cited

U.S. PATENT DOCUMENTS 5,723,333  3/1998  Levine et al. ........................... 435/325

FOREIGN PATENT DOCUMENTS

| | | |
|---|---|---|
| WO 92/13091 | 8/1992 | WIPO . |
| WO 94/18992 | 9/1994 | WIPO . |
| WO 95/05738 | 3/1995 | WIPO . |
| WO 95/11984 | 5/1995 | WIPO . |
| WO 95/12660 | 5/1995 | WIPO . |
| WO 95/13392 | 5/1995 | WIPO . |
| WO 95/27494 | 10/1995 | WIPO . |
| WO 95/28948 | 11/1995 | WIPO . |

OTHER PUBLICATIONS

Reed, *J. Cell Biol.*, vol. 125, Jan. 1994, pp. 1–6.
Klein et al., *EMBO J.* vol. 8, 1989, pp. 3701–3709.
Akli et al., "Transfer of a Foreign Gene into the Brain Using Adenovirus Vectors," *Nature Genet.* 3:224–228 (1993).
Barkats et al., "An Adenovirus Encoding CuZnSOD Protects Cultured Striatal Neurons Against Glutamate Toxicity," *Neuroreport*, 7:497–501 (1996).
Davidson et al., "A Model System for In Vivo Gene Transfer into the Central Nervous System Using an Adenoviral Vector," *Nature Genet.*, 3:219–223 (1993).
Durham et al. "Toxicity of Replication–Defective Adenoviral Recombinants in Dissociated Cultures of Nervous Tissue," *Exp. Neurol.*, 140:14–20 (1996).
Ghadge et al., "CNS Gene Delivery by Retrograde Transport of Recombinant Replication–Defective Adenoviruses," *Gene Ther.*, 2:132–137 (1995).
LaSalle et al., "An Adenovirus Vector for Gene Transfer into Neurons and Glia in the Brain," *Science*, 259:988–990 (1993).
Moriyoshi et al., "Labeling Neural Cells Using Adenoviral Gene Transfer of Membrane–Targeted GFP," *Neuron*, 16:255–260 (1996).
Paquet et al., "Proneuropeptide Y Processing in Large Dense–Core Vesicles: Manipulation of Prohormone Convertase Expression in Sympathetic Neurons Using Adenoviruses," *J. Neurosci.*, 16:964–973 (1996).
Slack et al., "Adenovirus–Mediated Gene Transfer of the Tumor Suppressor, p53, Induces Apoptosis in Postmitotic Neurons," *J. Cell Biol.*, 135:1–12 (1996).
Slack et al., "Viral Vectors for Modulating Gene Expression in Neurons," *Curr. Opin. Neurobiol.*, 6:576–583 (1996).
Wilkemeyer et al., "Adenovirus–Mediated Gene Transfer into Dissociated and Explant Cultures of Rat Hippocampal Neurons," *J. Neurosci. Res.*, 43:161–174 (1996).
PCT Interntional Search Report for International Application No. PCT/IB 97/01619 (1998).

*Primary Examiner*—James Ketter
*Attorney, Agent, or Firm*—Clark & Elbing, LLP

[57] ABSTRACT

A postmitotic neuron containing an adenovirus vector, the neuron having been infected with the adenovirus vector at a multiplicity of infection of approximately 10 to approximately 50, and expressing a gene product encoded by a DNA molecule contained within said vector.

31 Claims, 27 Drawing Sheets

SEQUENCE LISTING

<160> NUMBER OF SEQ ID NOS: 1

<210> SEQ ID NO 1
<211> LENGTH: 68
<212> TYPE: PRT
<213> ORGANISM: Rat rattus

<400> SEQUENCE: 1

Trp Arg His Leu Ala Gly Glu Leu Gly Tyr Gln Pro Glu His Ile Asp
 1               5                  10                  15

Ser Phe Thr His Glu Ala Cys Pro Val Arg Ala Leu Leu Ala Ser Trp
                20                  25                  30

Gly Ala Gln Asp Ser Ala Thr Leu Asp Ala Leu Leu Ala Ala Leu Arg
            35                  40                  45

Arg Ile Gln Arg Ala Asp Ile Val Glu Ser Leu Cys Ser Glu Ser Thr
        50                  55                  60

Ala Thr Ser Pro
65

POST-MITOTIC NEURONS CONTAINING ADENOVIRUS VECTORS THAT MODULATE APOPTOSIS AND GROWTH

CROSS REFERENCE TO RELATED APPLICATIONS

This application claims benefit to U.S. Provisional Application Ser. No. 60/031,057, filed Nov. 18, 1996.

FIELD OF THE INVENTION

The field of the invention is neurobiology.

BACKGROUND OF THE INVENTION

Programmed cell death (apoptosis) is an ongoing process in both the developing and the mature nervous system. In the developing nervous system, neurons undergo apoptosis unless they receive an adequate supply of neurotrophic substances from the target (for example, the muscle) that they innervate. In the mature nervous system, apoptosis occurs in the course of neurodegenerative diseases, such as Alzheimer's and Parkinson's Diseases, which progress slowly over long periods of time, and in acute neurological insults, such as a stroke. Understanding how apoptosis is regulated is, therefore, an important step toward developing effective treatments for neurodegenerative diseases and stroke.

Apoptosis can be induced in a number of different cell types by overexpression of a tumor suppressor gene called p53 (reviewed in Elledge et al., Bioessays 17:923–930, 1995; White, Genes Dev. 10:1–15, 1996). Following DNA damage, which may cause the cell to proliferate uncontrollably, p53 is expressed and helps to prevent tumor formation by activating the expression of other genes, such as the cyclin kinase inhibitor p21 (also known as WAF-1), which mediates cell cycle arrest and prevents the propagation of damaged DNA (Harper et al., Cell 75:805–816, 1993; Xiong et al., Nature 366:701–704, 1993). The cellular response to overexpression of p53 may vary however, depending on the cell type; instead of arresting cell growth, p53 overexpression may cause apoptosis (Katayose et al., Int. J. Oncol. 3:781–788, 1995; Picksley et al. Current Opin. Cell Biol. 6:853–858, 1994; White, supra). The precise mechanism by which p53 mediates apoptosis in tumor cells is not well understood, nor is it known whether p53 is directly involved in the apoptosis of postmitotic (i.e., non-proliferating) neurons.

Recently, a number of studies have demonstrated that adenovirus-based vectors can be used to transduce neurons of the CNS that have been placed in culture (Slack et al. Current Opin. Neurobiol., 6:576–583, 1996), but it is not known if these may vectors negatively impact the function of the recipient cell. If adenovirus-derived vectors are to be useful for modulating apoptosis in neurons, their influence on the biochemistry and physiology of the neuron must be understood.

SUMMARY OF THE INVENTION

The invention features a postmitotic neuron that contains an adenovirus vector that was applied to the neuron, under conditions (such as those described herein) that allow the neuron to be infected, at a multiplicity of infection of, preferably, 1 to 1000 MOI (multiplicity of infection), more preferably 1 to 500 MOI, and most preferably approximately 10 to approximately 50 MOI. The neuron can express a gene product encoded by a DNA molecule contained within the vector.

In one embodiment, the postmitotic neuron is infected while in tissue culture. In a second embodiment, the postmitotic neuron is infected in vivo. The invention also features methods for making the cell in vitro and in vivo. The adenovirus vector may be administered according to methods known to skilled artisans including intracerebrally, intraventricularly, intrathecally, transmucosally, intramuscularly, or subcutaneously. Preferably the adenovirus vector is applied intravascularly.

The gene product encoded by the DNA contained within the adenovirus vector can be a structural protein, an enzyme, a transcription factor, or a receptor, such as the low-affinity nerve growth factor (NGF) receptor p75, or the high-affinity NGF receptor Trk or other members of the Trk family, including TrkB, TrkC, NT-3, and NT-4/5. Preferably, the gene product is a tumor suppressor. Most preferably, the gene product is p53. Alternatively, or in addition, the adenovirus vector can contain DNA encoding a reporter or marker gene product. Preferably, the reporter gene is alkaline phosphatase, chloramphenicol acetyltransferase, lacZ, or green fluorescent protein.

The invention also features a method of inducing apoptosis in a postmitotic neuron by infecting the neuron with an adenoviral vector that contains DNA encoding a protein that induces apoptosis, such as p53. In addition, the invention features a method of inducing apoptosis in a postmitotic neuron by infecting the neuron with an adenoviral vector that contains DNA encoding a protein that inhibits apoptosis, such as Bcl-2, Bcl-XL, E1B55K, or Gab1.

The invention also features methods of identifying test compounds which inhibit or induce apoptosis, growth, or proliferation, the methods comprising comprising (a) culturing a population of postmitotic neurons; (b) infecting the neurons of said population with an adenovirus vector comprising DNA encoding a protein that induces (or inhibits) apoptosis (or growth or proliferation), said vector preferentially being applied to said neurons at a multiplicity of infection of approximately 10 to approximately 50; (c) exposing a subset of the population of neurons infected in step (b) to a test compound, said test compound being a candidate inhibitor (or inducer) of apoptosis, growth, or proliferation; and (d) comparing the approximate number of neurons that undergo apoptosis, growth, or proliferation, as appropriate, in the subset of the population that was infected and exposed to said test compound with the approximate number of neurons that undergo apoptosis, growth, or proliferation in the population of cells that were infected.

The invention may be practiced with DNA molecules that encode full-length proteins or fragments thereof that are biologically active. Similarly, the invention may be practiced with DNA molecules that differ from those described herein by one or more conservative amino acid substitutions. Preferably, the protein contains less than 50% substituted amino acid residues, more preferably less than 30% substituted amino acid residues, and most preferably less than 10% substituted amino acid residues.

By "biologically active" is meant possessing any in vivo or in vitro activity that is characteristic of the full-length protein. A biologically active fragment generally possesses at least 40%, more preferably at least 70%, and most preferably at least 90% of the activity of the full-length protein. Preferably, the fragment mimics at least one activity of the full length protein.

By "conservative amino acid substitution" is meant substitution within the following groups: glycine, alanine; valine, isoleucine, leucine; aspartic acid, glutamic acid;

asparagine, glutamine; serine, threonine; lysine, arginine; and phenylalanine, tyrosine.

By "apoptosis" is meant the process of cell death wherein a dying cell displays a set of well-characterized biochemical hallmarks which include cytolemmal membrane blebbing, cell soma shrinkage, chromatin condensation, and DNA laddering.

By "stimulus which is capable of inducing apoptosis" or "apoptotic stimulus" is meant any chemical or physical treatment which initiates apoptosis as defined above. For example, nerve growth factor withdrawal, hypoxia, exposure to staurosporine, and cerebral ischemia are stimuli capable of inducing apoptosis in neurons.

By "neuron" is meant a cell of ectodermal embryonic origin derived from any part of the nervous system of an animal. Neurons express well-characterized neuron-specific markers which include class III β-tubulin, MAP2, and neurofilament proteins. Neurons includes without limitation, hippocampal, cortical, midbrain dopaminergic, motor, sensory, and sympathetic neurons.

By "neuronal growth" is meant an increase in process network density of approximately 2-fold or greater, an increase in total neurite length of approximately 1.5-fold or greater, an increase in cell size (area) of approximately 10% or greater, preferably 25% or greater, an increase in Tα1 α-tubulin mRNA of approximately 5-fold or greater, and/or an increase in tyrosine hydroxylase mRNA of approximately 2-fold or greater.

By "expose" is meant to allow contact between an animal, cell, lysate or extract derived from a cell, or molecule derived from a cell, and a test compound or apoptotic stimulus.

By "treat" is meant to submit or subject an animal, cell, lysate or extract derived from a cell, or molecule derived from a cell to a test compound or apoptotic stimulus.

By "test compound" is meant a chemical, be it naturally-occurring or artificially-derived, that is surveyed for its ability to modulate cell death, by employing one of the assay methods described herein. Test compounds may include, for example, peptides, polypeptides, synthesized organic molecules, naturally occurring organic molecules, nucleic acid molecules, and components thereof.

By "assaying" is meant analyzing the effect of a treatment, be it chemical or physical, administered to whole animals or cells derived therefrom. The material being analyzed may be an animal, a cell, a lysate or extract derived from a cell, or a molecule derived from a cell. The analysis may be, for example, for the purpose of detecting altered gene expression, altered RNA stability, altered protein stability, altered protein levels, or altered protein biological activity. The means for analyzing may include, for example, antibody labeling, immunoprecipitation, phosphorylation assays, and methods known to those skilled in the art for detecting nucleic acids.

By "modulating" is meant changing, either by decrease or increase.

By "a decrease" is meant a lowering in the level of: a) protein, or protein phosphorylation, as measured by ELISA; b) reporter gene activity, of at least 30%, as measured by reporter gene assay, for example, lacZ/α-galactosidase, green fluorescent protein, luciferase, etc.; c) mRNA, levels of at least 30%, as measured by PCR relative to an internal control, for example, a "housekeeping" gene product such as α-actin or glyceraldehyde 3-phosphate dehydrogenase (GAPDH). In all cases, the lowering is preferably by 30%, more preferably by 40%, and even more preferably by 70%.

By "an increase" is meant a rise in the level of: a) protein, or protein phosphorylation, measured by ELISA; b) reporter gene activity, of as measured by reporter gene assay, for example, lacZ/α-galactosidase, green fluorescent protein, luciferase, etc.; c) mRNA, as measured by PCR relative to an internal control, for example, a "housekeeping" gene product such as β-actin or glyceraldehyde 3-phosphate dehydrogenase (GAPDH). Preferably, the increase is by 2-fold, more preferably 3-fold.

By "alteration in the level of gene expression" is meant a change in gene activity such that the amount of a product of the gene, i.e., mRNA or polypeptide, is increased or decreased, that the stability of the mRNA or the polypeptide is increased or decreased.

By "reporter gene" is meant any gene which encodes a product whose expression is detectable and/or quantitatable by immunological, chemical, biochemical or biological assays. A reporter gene product may, for example, have one of the following attributes, without restriction: fluorescence (e.g., green fluorescent protein), enzymatic activity (e.g., lacZ/α-galactosidase, luciferase, chloramphenicol acetyltransferase), toxicity (e.g., ricin A), or an ability to be specifically bound by a second molecule (e.g., biotin or a detectably labelled antibody). It is understood that any engineered variants of reporter genes, which are readily available to one skilled in the art, are also included, without restriction, in the forgoing definition.

By "operably linked" is meant that a gene and a regulatory sequence are connected in such a way as to permit expression of the gene product under the control of the regulatory sequence.

By a "transgene" is meant a nucleic acid sequence which is inserted by artifice into a cell and becomes a part of the genome of that cell and its progeny. Such a transgene may be partly or entirely heterologous to the cell.

By "transgenic animal" an animal comprising a transgene as described above.

By "protein" or "polypeptide" or "polypeptide fragment" is meant any chain of more than two amino acids, regardless of post-translational modification (e.g., glycosylation or phosphorylation), constituting all or part of a naturally-occurring polypeptide or peptide, or constituting a non-naturally occurring polypeptide or peptide.

All publications mentioned herein are incorporated by reference. Examples of the preferred methods and materials will now be described. These examples are illustrative only, and are not intended to be limiting. Those skilled in the art will understand that methods and materials similar or equivalent to those described here can be used in the practice or testing of the present invention.

BRIEF DESCRIPTION OF THE DRAWINGS

FIGS. 1(A–F) is a series of photographs illustrating the morphology of cultured sympathetic neurons following viral infection.

FIG. 4(A–D) are photographs illustrating changes in cytoarchitecture of sympathetic neurons following infection with recombinant adenovirus.

FIG. 7(A–C) are photographs showing Western blot analysis of p53 (FIGS. 7A and 7B) following transduction of sympathetic neurons and an agarose gel analysis of fragmented DNA (FIG. 7C).

FIGS. 15(A–B) are photographs illustrating in vivo-infected cells in the superior cervical ganglia.

DETAILED DESCRIPTION

Figure 1A:
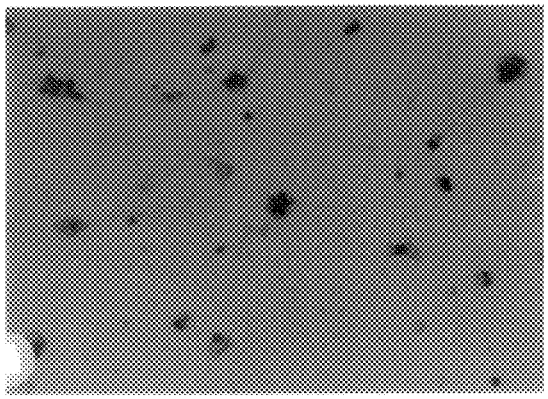
FIGS. 1A, 1C, and 1E are photographs of neurons infected with adenovirus at 1, 10, and 100 MOI, respectively.

The compositions and methods described herein provide a means of efficiently transfecting postmitotic cells, such as neurons, with adenovirus vectors. The vectors can be used to express useful genes, such as the tumor suppressor gene p53, and the growth factor receptor genes Trk and p75.

The assays described herein can be used to test for compounds that decrease cell death and/or stimulate cell growth and hence may have therapeutic value in the treatment of neurodegenerative disease and neurological trauma. The assays also can be used to screen compounds for inhibition of neural cell growth and/or for neurotoxicity, such compounds being useful as pesticides or cancer therapeutics, for example.

Secondary Screens of Test Compounds that Appear to Modulate Neuronal Death.

After test compounds that appear to have neuronal death and/or growth-modulating activity are identified, it may be necessary or desirable to subject these compounds to further testing. The invention provides such secondary confirmatory assays. For example, a compound that appears to inhibit neuronal death in early testing will be subject to additional assays to determine whether the compound can stimulate neuronal growth. At late stages testing will be performed in vivo to confirm that the compounds initially identified to affect cell death in cultured neurons will have the predicted effect on in vivo neurons. In the first round of in vivo testing, neuronal cell death is initiated in animals, by well-known methods such as axotomy or cerebral ischemia, and then the compound is administered by one of the means described in the Therapy section immediately below. Neurons or neural tissue are isolated within hours to days following the insult, and are subjected to assays as described in the examples below.

Test Compounds

In general, novel drugs for prevention or treatment of neuronal cell death or growth are identified from large libraries of both natural product or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, NH) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their therapeutic activities for neurodegenerative or neuroproliferative disorders should be employed whenever possible.

When a crude extract is found to prevent or decelerate neuronal death or proliferation, further fractionation of the positive lead extract is necessary to isolate chemical constituents responsible for the observed effect. Thus, the goal of the extraction, fractionation, and purification process is the careful characterization and identification of a chemical entity within the crude extract having neuronal apoptosis (or conversely, proliferation) -preventative or -palliative activities. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using a mammalian neuronal apoptosis or proliferation model as appropriate.

Below are examples of high-throughput systems useful for evaluating the efficacy of a molecule or compound in treating, preventing, or enhancing a neuronal apoptosis-associated or proliferation-associated condition.

Therapy

Compounds identified using any of the methods disclosed herein, may be administered to patients or experimental animals with a pharmaceutically-acceptable diluent, carrier, or excipient, in unit dosage form. Conventional pharmaceutical practice may be employed to provide suitable formulations or compositions to administer such compositions to patients or experimental animals. Although intravenous administration is preferred, any appropriate route of administration may be employed, for example, parenteral, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for antagonists or agonists of the invention include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Use of Primary Neurons Infected with Recombinant Adenoviral Vectors to Test Compounds for Their Effect on Neuronal Cell Death or Growth Primary neurons, for example, sympathetic neurons of the superior cervical ganglia, or cortical neurons, or neural progenitor cells, are cultured in 96-well tissue culture plates by standard methods. Cell death or growth is induced or inhibited by withdrawing or adding neuronal growth factors, or by infection with recombinant adenoviruses. For example, to induce cell death, neurons may be infected with an adenoviral vector encoding p53, as described in earlier examples. Concomitantly, compounds to be tested (for example, for the inhibition of p53-mediated cell death) are added to the cells in a range of concentrations. At appropriate timepoints, e.g., between 0 and 36 hours, the treated samples are lysed by standard techniques and the cell lysates are subjected to the appropriate assay as described below.

ELISA for the Detection of Compounds that Modulate Neuronal Cell Death and Growth Enzyme-linked immunosorbant assays (ELISAs) are easily incorporated into high-throughput screens designed to test large numbers of compounds for their ability to modulate levels of a given protein. When used in the methods of the invention, changes in a given protein level of a sample, relative to a control, reflect changes in the apoptotic or growth status of the cells within the sample. Protocols for ELISA may be found, for example, in Ausubel et al.,*Current Protocols in Molecular Biology*, John Wiley & Sons, New York, N.Y., 1997. Lysates from neuronal cells treated with potential cell death or growth modulators are prepared (see, for example, Ausubel et al., supra), and are loaded onto the wells of microtiter plates coated with "capture" antibodies against one of the neuronal health/growth markers discussed earlier, for example, T$\alpha$1 $\alpha$-tubulin or tyrosine hydroxylase. Unbound antigen is washed out, and a health/growth marker-specific antibody, coupled to an agent to allow for detection, is added. Agents allowing detection include alkaline phosphatase (which can be detected following addition of colorimetric substrates such as p-nitrophenolphosphate), horseradish peroxidase (which can be detected by chemiluminescent substrates such as ECL, commercially available from Amersham) or fluorescent compounds, such as FITC (which can be detected by fluorescence polarization or time-resolved fluorescence). The amount of antibody binding, and hence the level of a health/growth marker within a lysate sample, is easily quantitated on a microtiter plate reader.

As a baseline control for health/growth marker levels in non-dying cells, a sample that is continuously exposed to NGF is included. As a baseline control for health/growth marker levels in dying cells, a sample in which NGF is withdrawn and not replaced is included. As a baseline control for health/growth marker levels in growing cells, a sample that is continuously to NGF, and then to which an neurotrophin such as NT-3 (see Example X, Assays for Neuronal Growth) is included. MAP kinases and the p85 subunit of PI3 kinase are used as internal standards for absolute protein levels, since their levels do not change over the preferred timecourse (0 to 36 hours after NGF withdrawal). A positive assay result, for example, identification of a compound that decreases p53-mediated neuronal apoptosis, is indicated by an increase in health/growth marker levels (such as T$\alpha$1 $\alpha$-tubulin), relative to the health/growth marker level observed in cells which are induced to die without rescue.

Reporter Gene Assays for Compounds that Modulate Neuronal Cell Death and Growth

Assays employing the detection of reporter gene products are extremely sensitive and readily amenable to automation, hence making them ideal for the design of high-throughput screens. Assays for reporter genes may employ, for example, colorimetric, chemiluminescent, or fluorometric detection of reporter gene products. Many varieties of plasmid and viral vectors containing reporter gene cassettes are easily obtained. Such vectors contain cassettes encoding reporter genes such as lacZ/$\beta$-galactosidase, green fluorescent protein, and luciferase, among others. Cloned DNA fragments encoding transcriptional control regions of interest are easily inserted, by DNA subcloning, into such reporter vectors, thereby placing a vector-encoded reporter gene under the transcriptional control of any gene promoter of interest. The transcriptional activity of a promoter operatively linked to a reporter gene can then be directly observed and quantitated as a function of reporter gene activity in a reporter gene assay.

Reporter Gene Assay of Primary Neurons from Transgenic Mice

Primary neurons from mice containing one or more reporter transgene constructs are cultured, cell death or growth is induced or inhibited, and compounds to be tested for their death/growth -modulating activity are added to the neurons. At appropriate timepoints, cells are lysed and subjected to the appropriate reporter assays, for example, a calorimetric or chemiluminescent enzymatic assay for lacZ/$\beta$-galactosidase activity, or fluorescent detection of GFP. Changes in reporter gene activity of samples treated with test compounds, relative to reporter gene activity of appropriate control samples as suggested in the previous section, indicate the presence of a compound that modulates neuronal cell death.

In one embodiment, one transgene could comprise a reporter gene such as lacZ or green fluorescent protein (GFP), operatively linked to a promoter from a health/growth marker gene such as the neuron-specific Tα1 α-tubulin gene (see, e.g., U.S. Pat. No. 08/215,083). The Tα1 α-tubulin gene is abundantly expressed in developing neurons during morphological growth, and also is abundantly expressed in mature neurons during the process of target re-innervation. Hence, the amount of activity resulting from a reporter gene that is operatively linked to the Tα1 α-tubulin promoter will indicate the proportion of live (or growing) neurons within a sample, relative to the appropriate controls. Transgenes may be present within the genomic DNA of a neuron to be tested, or may be transiently introduced into a neuron. A second transgene, comprising a second reporter gene operatively linked to a second promoter, is included as an internal control. This could be a reporter gene operatively linked, for example, to the neuron-specific T26 α-tubulin promoter, which is constitutively expressed in neurons, or alternatively, a promoter from a housekeeping gene known to those skilled in the art, for example, GAPDH.

Reporter Gene Assay in Adenovirus-transduced Primary Neurons

Primary neurons from transgenic or non-transgenic animals are isolated and infected with an adenovirus containing a reporter gene construct of interest, such as those described immediately above. The neurons are treated with test compounds, apoptosis or growth is initiated or inhibited, and reporter activity is measured and interpreted as provided herein.

Alternatively, a gene whose expression modulates neuronal cell death or growth can be introduced by adenovirus-mediated gene transfer, as discussed above. For example, an oncogene that stimulates neurons to proliferate uncontrollably may be introduced into Tα1 α-tubulin:nlacZ-expressing neurons by adenovirus-mediated gene transfer. Expression of the adenoviral vector-encoded oncogene induces cells to proliferate, and in this manner, test compounds that specifically interfere with neural proliferation can be isolated. For example, a desirable result in a screen for a compound that specifically inhibits proliferating neurons, but does not induce death in postmitotic neurons, would be a compound that decreases health/growth reporter gene (e.g. Tα1 α-tubulin:nlacZ) expression in oncogene-expressing, proliferating neurons, but does not alter reporter gene expression in normal postmitotic neurons. Conversely, screens for compounds that promote neuronal growth, or inhibit neuronal death, may be performed using analogous approaches.

Quantitative PCR of Health/growth Marker mRNA as an Assay for Compounds that Modulate Neuronal Cell Death and Growth The polymerase chain reaction (PCR), when coupled to a preceding reverse transcription step (rtPCR), is a commonly used method for detecting vanishingly small quantities of a target mRNA. When performed within the linear range, with an appropriate internal control target (employing, for example, a housekeeping gene such as actin), such quantitative PCR provides an extremely precise and sensitive means of detecting slight modulations in mRNA levels. Moreover, this assay is easily performed in a 96-well formnat, and hence is easily incorporated into a high-throughput screening assay. Neurons are cultured, treated with test compounds, and growth or death is induced or inhibited as described in the preceding examples. The neurons are then lysed, the mRNA is reverse-transcribed, and the PCR is performed according to commonly used methods, (such as those described in Ausubel et al., *Current Protocols in Molecular Biology*, John Wiley & Sons, New York, N.Y., 1997), using oligonucleotide primers that specifically hybridize with the nucleic acid of interest. In one embodiment, the target mRNA could be that of one or more of the health/growth markers, such as Tα1 α-tubulin, or tyrosine hydroxylase.

Summary

The data presented in the examples hereinbelow support several conclusions. The first is that adenovirus-derived vectors can be effectively used as gene transfer agents for postmitotic neurons. When used between 10 and 50 MOI, recombinant adenovirus can infect more than 75% of sympathetic neurons with little perturbation in cell survival, cytoarchitecture, or physiological function for at least 7 days. A second conclusion is that, within the parameters defined with the AdSCA17LacZ recombinant adenovirus, overexpression of p53 is sufficient to induce apoptosis in postmitotic neurons. Moreover, p53-mediated cell death can be inhibited by recombinant adenoviruses expressing inhibitors of p53, such as E1B55K, and Bcl-2. In addition, neuronal survival can be mediated adenoviruses encoding proteins such as Gab-1, and growth factor receptors, such as TrkB.

The first conclusion demonstrates the utility of recombinant adenoviral vectors in mechanistic studies of postmitotic neurons, particularly when these studies are performed using the parameters discussed herein. At titres in excess of 100 MOI, assays of mitochondrial function indicate a decrease in cell survival. Cells surviving excessive infection rates exhibited remarkable changes in the nuclear ultrastructure including electron dense inclusions, filamentous aggregates and, in severe cases, disintegration of chromatin. Pathological changes resulting from recombinant viral transduction warrants further investigation, particularly with regard to viral-mediated gene therapy.

The second conclusion has major implications for the mechanisms of cell death that occurs in the nervous system in the event of a progressive disease or a sudden stroke. Since these data indicate that endogenous p53 is stably expressed in SCG neurons, it appears that the protein must be expressed at a given threshold level before the apoptotic pathway is triggered. Once this threshold is reached, p53 alone is sufficient to induce neuronal apoptotic cell death. Thus, upregulation of p53 following neuronal injury may be the key signal leading to the demise of injured neurons. Future studies employing adenovirus-derived vectors to introduce p53 deletion mutants will help to define the mechanism of p53 action in postmitotic neurons. In addition, recombinant adenoviruses encoding proteins that inhibit p53 activity may be useful as therapeutic inhibitors of apoptosis in post-mitotic neurons. Furthermore, neurons expressing adenovirus vector-encoded proteins will be a useful tool to screen for therapeutic compounds that regulate neuronal death and proliferation.

EXAMPLE I

GENERAL METHODS

Viral Vectors

Ad5CA17LacZ

The adenoviral recombinant carrying an *E. coli* β-galactosidase expression cassette with a CMV promoter (Ad5CA17LacZ) was generated by the cotransfection of pCA14(lacZ) and pJM17 as previously described (Bett et al., Proc. Natl. Acad. Sci. USA 91:8802–8806, 1994). This E1- and E3-deleted virus contains the reporter gene in the E1 region.

p53-expressing and mutant E1A (Ad1101)-expressing recombinant adenovirus

A recombinant adenovirus carrying wild-type human p53 was constructed according to the method of Graham (Bett et al., supra; see also Katayosc et al., Cell Growth Diff. 6:1207–1212, 1995). The results obtained with this vector were verified with a second preparation of adenovirus vector that also confers p53 expression, AdWTp53 (Bacchetti et al., Int. J. Oncol. 3:781–788, 1993). The adenovirus vector carrying the p300-binding mutant (Ad1101) of E1A was on a 12S lacking E1B (Jelsma et al., Virology 163:494–502, 1988).

Recombinant adenoviruses were amplified on 293 cells, a human embryo kidney cell line, expressing the adenovirus type 5 E1A and E1B proteins (Graham et al., In Methods in Molecular Biol. E. J. Murray, Ed., The Humana Press, pages 109–128). These vectors were harvested from cell lysates and either used directly or further purified on CsCl gradients according to Graham et al.(supra). Infectious titre was determined by plaque assay on 293 cells (also as described by Graham et al., supra).

When comparing the effects of adenovirus-mediated p53 or E1A (Ad1101) overexpression versus β-galactosidase overexpression, the following steps were taken in order to ensure that the observations made were not attributable to differences in viral preparations: (1) all viral preparations were purified in an identical manner; (2) several preparations of each virus were examined; (3) particle content of each viral preparation, which is a potential source of cytotoxicity, was in a similar range; and (4) results were reproduced with four different adenovirus recombinants; two expressing lacZ and two expressing p53. Particle content was determined by obtaining the ratio of infectious titre to titre at an optical density of 260 nm, according to standard procedures (Bett et al., supra). The ratio of infectious titre to particle content are typically approximately 1:100. The ratios obtained for the lacZ and p53 adenovirus recombinants were found to be in this range, at 1:110 and 1:120, respectively.

Recently, the emergence of E1 -containing, replication-competent virus contamination in stocks of replication-defective adenovirus has been noted following serial passage (Lochmuller et al., Hum. Gene Therapy 5:1485–1491, 1994). To verify the purity of virus stocks, both PCR and Southern blot analysis were performed; these procedures are capable of detecting any contaminating E1-containing virus. For PCR analysis, recombinant viral DNA was extracted and amplified with primers specific for the E1 region (Lochmuller et al., supra). DNA that was purified from wild-type virus was used as a positive control. When wild-type contamination was detected by PCR analysis, Southern blots of wild-type and recombinant viral DNAs were prepared and probed with radiolabelled DNA fragments that would hybridize with the E1 and E2 region of the viral genome (Lochmuller et al., supra). For pure preparations, hybridization with a probe for the E1 region should reveal a positive signal in wild-type virus only, while the probe for E2, a region present in both recombinant and wild-type virus, should produce a single band indicating a pure population of virus in both DNA preparations. If traces of wild-type contamination were detected, recombinant viruses were further plaque purified according to Graham et al. (supra).

RH105

The HSV vector, RH105, carries the *E. coli* lacZ gene inserted in the thymidine kinase (TK) gene, upstream of the immediate early promoter ICP4 (Ho et al., Virol. 174:279–283, 1988). The disrupted TK gene renders the virus replication incompetent in postmitotic cells such as neurons (Boviatsis et al., Human Gene Therapy 5:183–191, 1994; Don et al., Proc. Natl. Acad. Sci. USA 88:1157–1161, 1991; Lipson et al., Proc. Natl. Acad. Sci. USA 86:6848–6852; Sherley et al., J. Biol. Chem. 263:8350–8358, 1988). The virus was propagated on Vero cells until a 100% cytopathic effect was observed, after which time cells were freeze-thawed and sonicated on ice to release virus particles. Large cell debris was removed by centrifugation at 1800×g for 10 minutes. The resulting supernatant was then layered on a 25% sucrose cushion in phosphate-buffered saline (PBS) and centrifuged at 70,000×g for 18 hours. The pellet containing recombinant Herpes Virus was resuspended in PBS and titred on Vero cells. The absence of wild-type virus was confirmed by X-gal staining of plaques generated on Vero cells.

Multiplicity of infection (MOI) was calculated based on titration on 293 cells for adenovirus-based vectors and on Vero cells for the HSV RH105 vector, and represents the number of plaque forming units added per cell.

To determine directly if p53 induction is sufficient to trigger the onset of apoptosis in postmitotic neurons, a recombinant adenovirus vector was used to deliver p53 to cultured sympathetic neurons. The efficacy of adenoviral vectors as gene transfer agents to sympathetic neurons was evaluated, and the parameters within which these vectors can be effectively used were defined. As described below, a recombinant adenovirus carrying the lacZ reporter gene inserted in the deleted E1 region (Bett et al., Proc. Natl. Acad. Sci., USA 91:8802–8806, 1994) was used to transduce sympathetic neurons from the superior cervical ganglia in vitro. Examination of infectivity, cytotoxicity, cell physiology, and cytoarchitecture indicated that such adenovirus recombinants have the potential to serve as highly effective gene transfer agents to sympathetic neurons. Working within the parameters defined, a wild-type human p53 expression cassette was introduced into the same vector backbone and used to transduce cultured sympathetic neurons. Overexpression of p53 mediated apoptosis in these neurons. The demonstration that p53 is sufficient to induce apoptosis in postmitotic neurons has major implications for the mechanisms of cell death in the traumatized mature nervous system.

Cell Survival Assays

To assay cell survival three different assays were used, including Live/Dead staining, TUNEL-labeling, and a quantitative MTT assay. For the Live/Dead staining the Live/Dead viability/cytotoxicity Kit (Molecular Probes) was used according to the manufacturer's instructions. Briefly, two reagents, calcein-AM and ethidium bromide, were added to cultures in their usual media. The calcein-AM is metabolically converted by intracellular esterase activity, resulting in the production of a green fluorescent product, calcein, an indicator of cell viability. Ethidium bromide is excluded from live cells, but is readily taken up by dead cells and stains the DNA. Cells are incubated in these reagents for 10 to 15 minutes at 37° C., after which time they are examined and photographed immediately, due to toxicity of these reagents.

To detect apoptosis, terminal transferase was used to visualize fragmented DNA (TUNEL-labeling). Parallel cultures were infected with Ad 1101 or AdlacZ at 25 MOI. After 72 hours, cells were fixed in acetone/methanol (1:1) for 10 minutes at −20° C. Fifty µl of a cocktail consisting of 1.0 µl biotin dUTP, 1.5 µl terminal transferase, 20 µl of 5× TdT buffer, and 78 µl distilled water was added to each coverslip. After a 1 hour incubation at 37° C., samples were washed three times in PBS, pH 7.4, and once in TBS, pH 8.0, to stop the reaction. Samples were incubated with a streptavidin CY3 diluted at 1:2,000 for 30 minutes. After 3×5-minute washes in PBS, samples were examined with an inverted fluorescent microscope.

For a quantitative measure of cell survival, the MTT survival assay (Cell Titre Kit, Promega, Madison, WI) was used as previously described (Slack et al., *J. Cell Biol.* 135:1085, 1996). This assay measures the mitochondrial conversion of the tetrazolium salt to a blue formizan salt, the accumulation of which can be measured colorimetrically.

Morphological Assays for Neuronal Growth:
Analysis and Quantification of Process Outgrowth, Neurite Length, and Cell Body Area Morphological assays for screening neuronal growth, for example assays that measure total neurite length, cell size, and neuronal process network density, are well known to those skilled in the art. Protocols for such assays may be found, for example, in Belliveau et al., *J. Cell Biol.* 136:375–388, 1997.

Analysis of the effects of neurotrophins and other treatments, such as infection with recombinant adenoviruses, on neuronal growth is examined by measuring three parameters: process network density, total neurite length, and cell body area. The quantitative analysis of cell process density on high and low density cultures was performed using common statistics applied to random sets of lines, in particular the number of intersection points per unit area. In the microscope, the network of neural processes appears as a random set of lines in a plane. The number of visible cross-links and bifurcations of cell processes per unit area can therefore be considered as a quantitative measure of the cell process density. However, since the number of neurites is a direct function of the number of neurons, only those regions in the culture having a similar cell density are comparable. Thus, in each experiment, 10–15 sampling windows (10 mm$^2$) were analyzed, each containing seven neuronal cell bodies. All interceptions and bifurcations of neurites within these windows were counted, resulting in an estimated value of neuritic process density. Statistical comparison of the mean values of density was performed using ANOVA (F-test).

Total neurite length and cell body area were measured in low density cultures within defined areas controlled for cell body number. Results were analyzed both within groups of sister cultures with different treatments and by pooling results of similar treatments from different groups of sister cultures. Similar results were obtained, and the pooled data are therefore presented. The t test and ANOVA were used to determine statistical significance.

Gene Expression Assays for Neuronal Growth

The growth of primary neurons expressing recombinant adenoviruses may be monitored via various gene expression assays that are well-known to those who are skilled in the art.

Sympathetic neurons can be grown under conditions in which their survival is maintained, for example, 10 ng/ml of NGF, infected with recombinant adenoviruses, and assayed for transcriptional increases in growth marker genes. Genes that serve as markers for neuronal growth, for example, tyrosine hydroxylase and Tα1 α-tubulin, show increase transcriptional activity in healthy versus unhealthy (or dying) neurons. Moreover, these growth marker genes display still more transcriptional activity in actively growing, versus quiescent, neurons. Hence, growth marker genes provide a simple and reliable method of monitoring neuronal growth.

Reporter gene assays also may be used to monitor neuronal growth. For example, we have generated transgenic mice containing chimeric transgenes that consist of a nuclear-localized lacZ coding region under the transcriptional regulation of the Tα1 α-tubulin promoter region. Expression of the Tα1 α-tubulin:nlacZ transgene in cultured sympathetic and cortical neurons from Tα1 α-tubulin:nlacZ transgenic mice is proportional to neuronal growth. Hence, lacZ assays may be used to monitor the health and growth of Tα1 α-tubulin:nlacZ transgenic neurons infected with recombinant adenoviruses. Alternatively, a recombinant adenoviral vector carrying a Tα1 α-tubulin:nlacZ reporter gene, or an analogous reporter gene, may be used to infect neurons in order to monitor their health and growth.

Gene Expression Assay for Neuronal Phenotype

Expression of recombinant adenovirus-encoded genes may be employed to alter the phenotype of a neuron. A gene expression assay is performed to determine or confirm the phenotype of the resulting transgenic neurons, which then are used as cellular therapeutics for various neurodegenerative diseases, or alternatively, in assays for the isolation of novel neurotherapeutic compounds.

For example, it would be desirable to have a reliable, abundant source of dopaminergic neurons: such neurons would be useful for screening assays, and for implantation into the brains of patients suffering from Parkinson's disease. The dopaminergic neurotransmitter phenotype of cultured neurons expressing a recombinant adenovirus-encoded protein is confirmed by assaying for tyrosine hydroxylase expression, for example, by monitoring mRNA levels by Northern hybridization or by reverse transcriptase/polymerase chain reaction, by methods known to those skilled in the art.

EXAMPLE II

NEURONAL GENE TRANSFER EFFICIENCY OF RECOMBINANT ADENOVIRUS VERSUS HERPES SIMPLEX VIRUS (HSV-1)

To determine the most effective and nontoxic gene transfer vector for postmitotic sympathetic neurons, parallel studies were initially conducted with the adenovirus vector Ad5CA17LacZ and the herpes simplex virus-1 vector RH105, which both, as described above, express the *E. coli* lacZ reporter gene. Pure cultures of neonatal sympathetic neurons were prepared and infected with replication defective viruses of both types as follows.

Cell Culture

Mass cultures of purified sympathetic neurons were prepared according to the procedure of Ma et al. (*J. Cell Biol.*) 117:135–141, 1992). Superior cervical ganglia were removed from newborn Sprague-Dawley rat pups (Charles River Laboratories, Charles River Canada, St. Constant, Quebec) and collected in L15 medium without sodium bicarbonate. The ganglia were washed in PBS (pH 7.4) and treated with 0.1% trypsin (Calbiochem Novabiochem, San Diego, Calif.) at 37° C. for 20 minutes, followed by treatment with DNase (10 pg/ml; Sigma Chemical Co., St. Louis, Mo.) for 2 minutes. Ganglia were triturated and passed through a 40 μm mesh (Becton-Dickinson Canada Inc. Mississauga, Ontario) to yield a single cell suspension. Following centrifugation in a clinical centrifuge, the pellet was resuspended in L15 medium supplemented with sodium bicarbonate (30 mM), vitamin C (1 mg/ml), cytosine arabinoside (10 μM), 3% rat serum, and 50 ng/ml NGF (Cedarlane Laboratories, Hornby, Ontario). Cells were plated at a density of 100,000 cells per ml of medium on tissue culture dishes that were coated with rat tail collagen. These cells are essentially free of non-neuronal cells (see also Ma et al., supra). The neurons were cultured for 3 to 5 days prior to viral infection, during which time they adhered to the culture dishes and extended processes.

For viral infection, medium was removed and replaced with 25% of the usual volume containing the appropriate titre of virus. Cells were incubated for 1 hour at 37° C., and the dishes were rocked every 15 minutes. The remaining 75% volume of medium was then added to each dish. For long-term cultures, medium was changed every 3 days.

Forty-eight hours after infection, the infected cultures were stained with X-gal to visualize β-galactosidase expression, which is encoded by the transgene.

Detection of β-Galactosidase Positive Cells

Staining for expression of β-galactosidase, the product of the lacZ reporter gene, was performed at various times following infection, as described throughout the Examples. Cells were fixed with 0.2% glutaraldehyde in PBS (pH 7.4) for 15 minutes at 4° C. Following the washes with PBS, cells were incubated for 18 hours in X-gal stain (2 mM $MgC_{12}$, 1 mg/ml X-gal, 5 mM $K_3Fe(CN)_6$, and 5 mM $K_4Fe(CN)_6$ in PBS (pH 7.4). To estimate the percentage of cells that were infected, the total cell number of cells and the number of lacZ positive cells were counted in 5 random fields. The data are expressed as the average of two separate experiments, with error bars representing the range. The number of cells per field was 125±50 for experiment 1, and 200±59 for experiment 2.

Figure 1B:
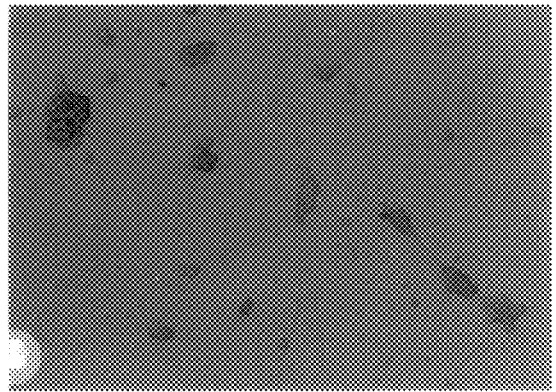
FIGS. 1B, 1D, and 1F are photographs of neurons infected with herpes virus at 1, 10, and 100 MOI, respectively. The bar in FIG. 1D represents 200 μm, and the bar in FIG. 1F represents 80 μm.
Figure 1C:
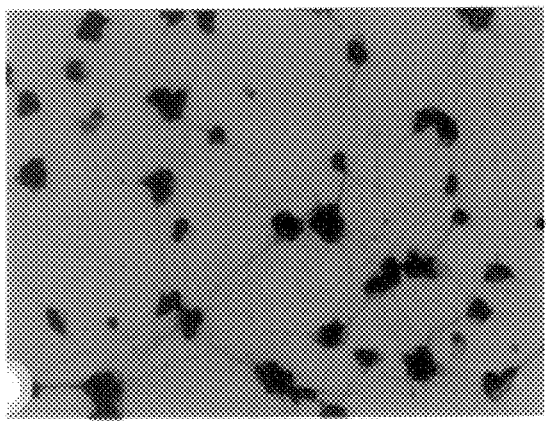
Figure 1D:
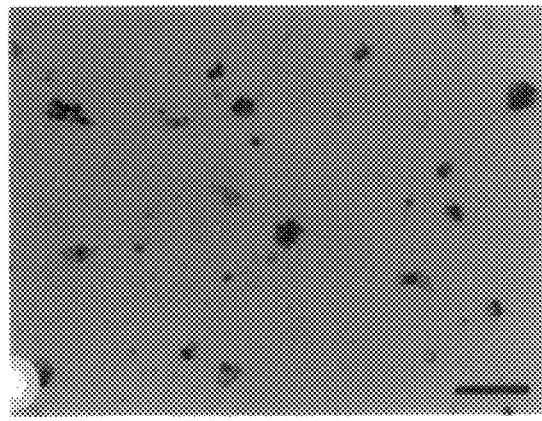
Figure 1E:
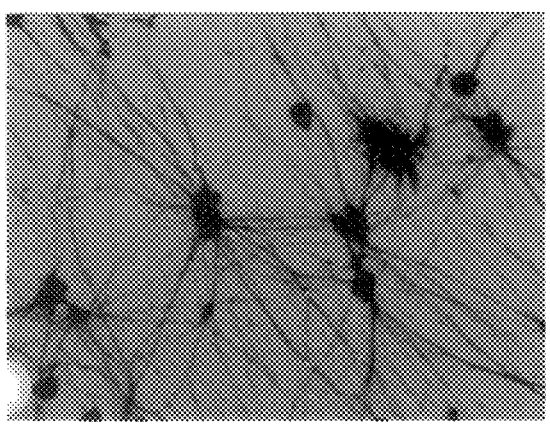
Figure 1F:
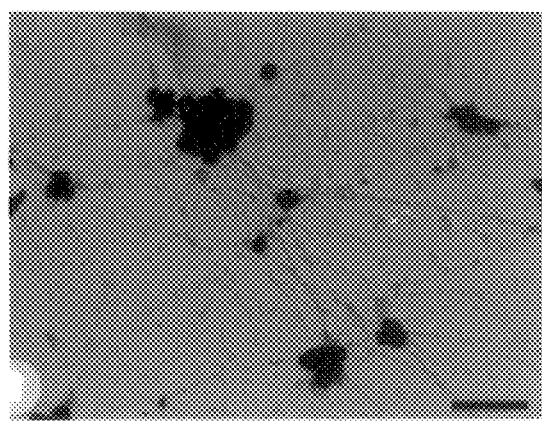

These experiments demonstrate that both HSV- and adenovirus-derived vectors are able to transduce sympathetic neurons in vitro. Closer examination of lacZ staining and cell morphology, however, indicated clear differences in the efficacy of these two vectors. At titres of 1 MOI, adenovirus infection led to a higher proportion of lacZ-positive neurons; compare FIG. 1A, a photograph of cultured sympathetic neurons infected with adenovirus at 1 MOI, with FIG. 1B, a photograph of the same type of cultured cells infected with herpes virus (HSV-1) at 1 MOI. At MOI's of 10, virtually all of the adenovirus infected neurons expressed the transgene (FIG. 1C) whereas many neurons in the HSV-1 infected cultures were negative (FIG. 1D). At the highest titre examined, 100 MOI, neurons infected with adenovirus recombinants appeared normal morphologically, exhibited no indication of cytotoxicity, and expressed the transgene at levels that were high enough to produce staining in both the cell bodies and the extended processes (FIG. 1E). In contrast, neurons infected with the HSV vector at 100 MOI displayed signs of severe degeneration, particularly of the neuritic processes, within 48 hours (FIG. 1F).

Figure 2A:
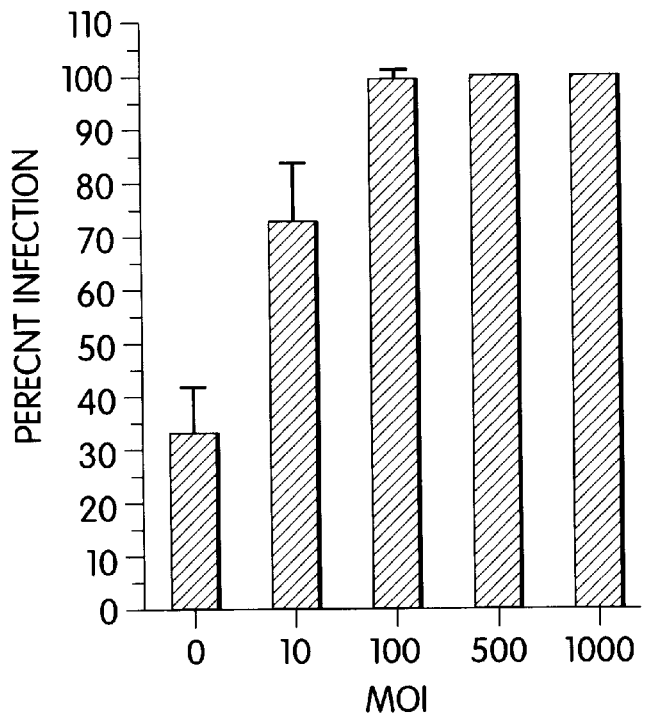
FIGS. 2(A–B) are bar graphs in which the infectivity of recombinant adenovirus and HSV-1 is compared. The percentage of neurons infected with recombinant adenovirus at 1–1000 MOI is shown in FIG. 2A, and the percentage of neurons infected with recombinant HSV-1 at 0.1–400 MOI is shown in FIG. 2B. The data are expressed as the average of two separate experiments; error bars represent the range. The number of cells per field was 125±50 for experiment 1, and 200±59 for experiment 2. The data obtained in these two experiments were averaged to give the result shown in FIG. 2.
Figure 2B:
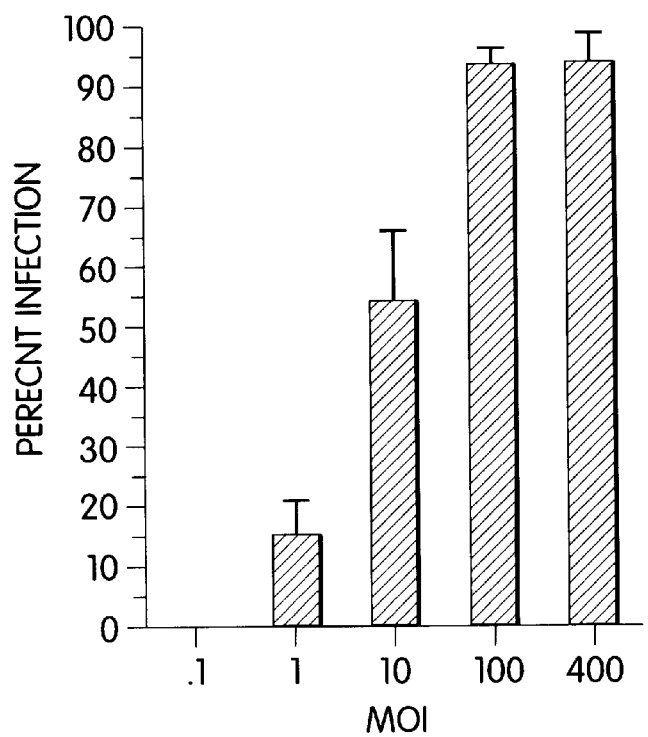

Quantitation of the number of lacZ-positive cells in sister cultures of sympathetic neurons infected with these two viral vectors confirmed the qualitative conclusions drawn from observing cultures such as those shown in FIG. 1. To obtain an estimate of the percentage of cells that were infected with each type of virus, the total number of cells and the number of lacZ-positive cells were counted in five random fields, as described above. Approximately 30% of sympathetic neurons were lacZ-positive following recombinant adenovirus infection at titres of 1 pfu/cell (FIG. 2A), but only 10% of the cells that were transduced by the HSV vector were positive at a similar titre (FIG. 2B). At 10 pfu/cell, transduction efficiency was again higher with adenovirus than with the HSV-1 vector, with 75% and 50% lacZ-positive cells in the sister cultures, respectively (FIGS. 2A and 2B). Titres of 100 pfu/cell or greater, with either vector, resulted in transduction of more than 95% of the cells, but the HSV-1 vector, at these MOIs, appeared to be cytotoxic. Therefore, cell survival was assessed following infection with these two different vectors.

EXAMPLE III

NEURONAL SURVIVAL FOLLOWING INFECTION WITH A RECOMBINANT ADENOVIRAL VECTOR

To assess potential cytotoxicity in response to viral infection, sympathetic neurons were infected with the adenoviral vector Ad5CA17LacZ or the HSV-1 vector RH105, and cell viability, as reflected by mitochondrial function, was assayed 2–10 days later.

Cell Survival Assay

Figure 3:
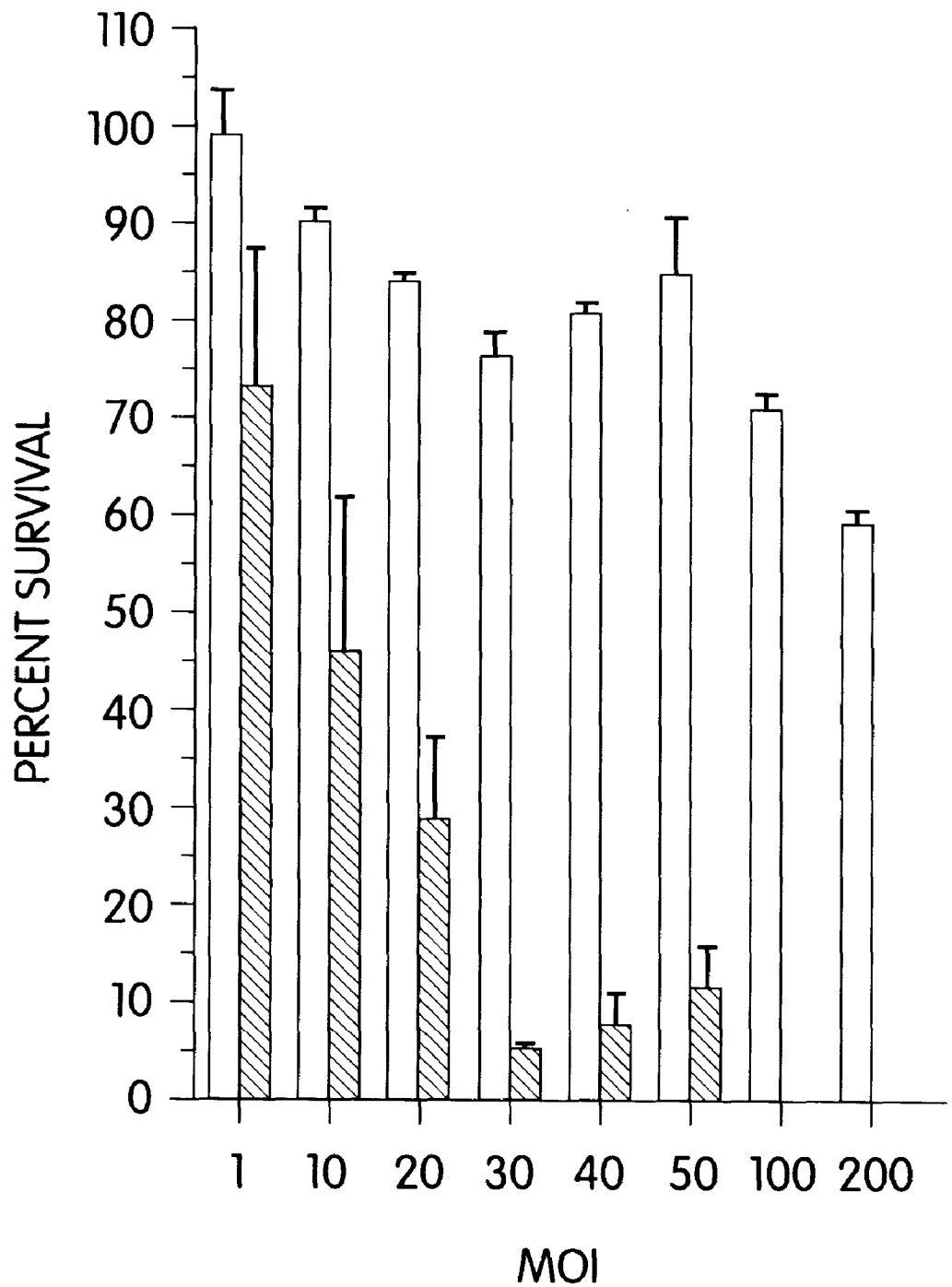
FIG. 3 is a bar graph in which neuronal viability is compared following infection with recombinant adenovirus and with HSV-1. The percentage of sympathetic neurons that survived after infection with recombinant adenovirus is shown by solid black bars, and the percentage surviving infection with recombinant HSV-1 is shown by hatched bars. The bars represent the mean of 3 separate samples ± SEM.

To assess cell survival, neurons were seeded at a density of 5,000 cells per well in 48-well tissue culture dishes and infected with varying titres of either adenovirus or HSV-1 vectors as described herein. Cell viability was measured by the metabolic conversion of a tetrazolium salt to formazan salt according to the CellTiter 96 Assay Kit™ (Promega, Madison, Wis.). As shown in FIG. 3, at 1 MOI there was no significant difference in the percentage of cells that survived following infection with recombinant adenovirus versus infection with recombinant HSV-1. However, as titres were increased, a large difference in cell survival was evident; at 10 MOI, 90% of the neurons in the adenovirus-infected cultures remained alive whereas only 45% of those in the HSV-infected cultures were alive. When these values were corrected for infectivity, almost all cells transduced with the HSV vector were lost following 10 days in culture (for example, at 10 MOI HSV, 55% of cells were infected and 55% of cells were lost). In contrast, when adenovirus-infected neurons were corrected for infectivity (i.e. 75% infected/10% lost) only 13% of infected cells were lost 10 days after infection at 10 MOI. A more striking difference appeared at 50 MOI; at this level of infection, the majority of the neurons in the HSV-infected cultures were lost (90%) while in adenovirus-infected cultures only 15% of neurons were lost. Therefore, HSV-1 has a relatively narrow effective range, and titres necessary to transduce greater than 75% of the cell population exhibit severe cytotoxic effects. The results indicate that adenovirus, at titres of 10 to 50 MOI, can transduce more than 70% of cells with minimal cytotoxicity for at least 10 days. Therefore, all of the experimentation described in the Examples below was carried out with adenovirus-based vectors.

EXAMPLE IV

CYTOARCHITECTURE OF TRANSDUCED NEURONS

While the cells appeared to have a normal morphology and continued to survive following infection with adenoviral recombinants, electron microscopy was carried out at 7 days postinfection to determine if the presence of a nonlytic virus carrying the lacZ reporter gene caused ultrastructural changes in surviving neurons.

Electron Microscopy

Sympathetic neurons were infected with the recombinant adenovirus Ad5CA17LacZ at titres of 0, 10, 50, 100 and 500 MOI. After 7 days in culture, cells were fixed with 1.5% glutaraldehyde in 0.1 M cacodylate buffer (pH 7.2) for 2 hours. In some experiments, neurons were infected with Adwtp53 at 50 MOI for 2 days, and fixed in the same manner. After initial fixation, samples were washed three times in 0.1 M sodium cacodylate buffer, for 15 minutes each wash. Specimens were postfixed on ice in 1% osmium tetroxide for 90 minutes, dehydrated in ascending concentrations of ethanol and acetone, and embedded in Epon-Araldite. Thin sections were cut, stained with uranyl acetate and lead citrate, and examined with a Hitachi H-7100 transmission electron microscope. Three separate grids containing 40 to 60 cells were examined for each specimen.

Figure 4A:
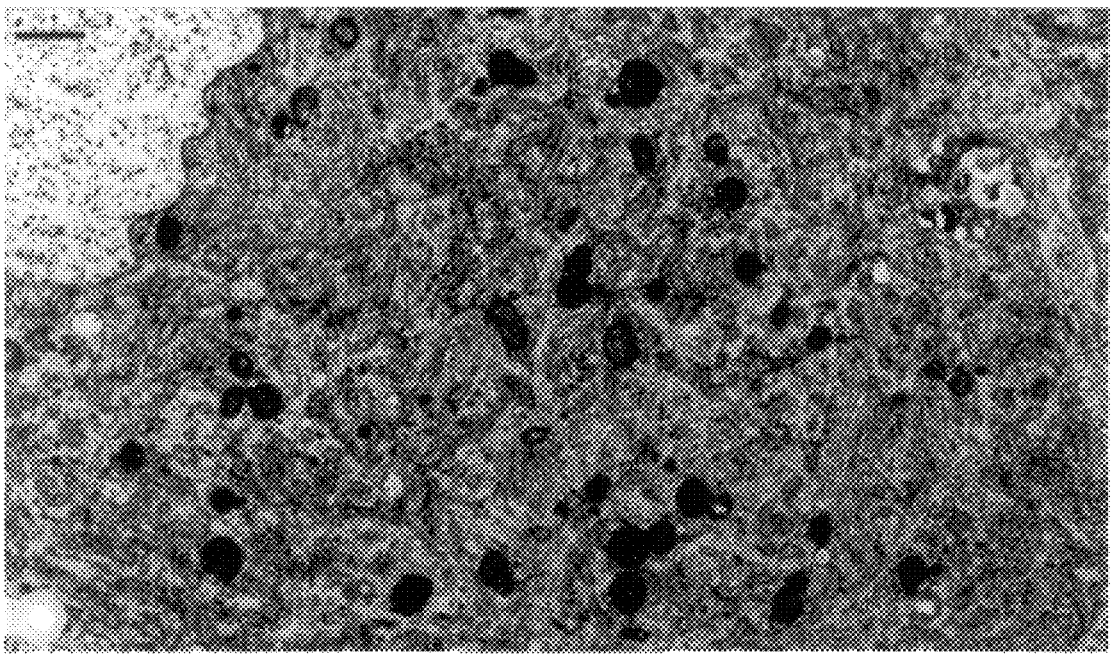
FIG. 4A shows an uninfected sympathetic neuron, which has normal cytoarchitecture (scale bar=0.3 $\mu$m).
Figure 4B:
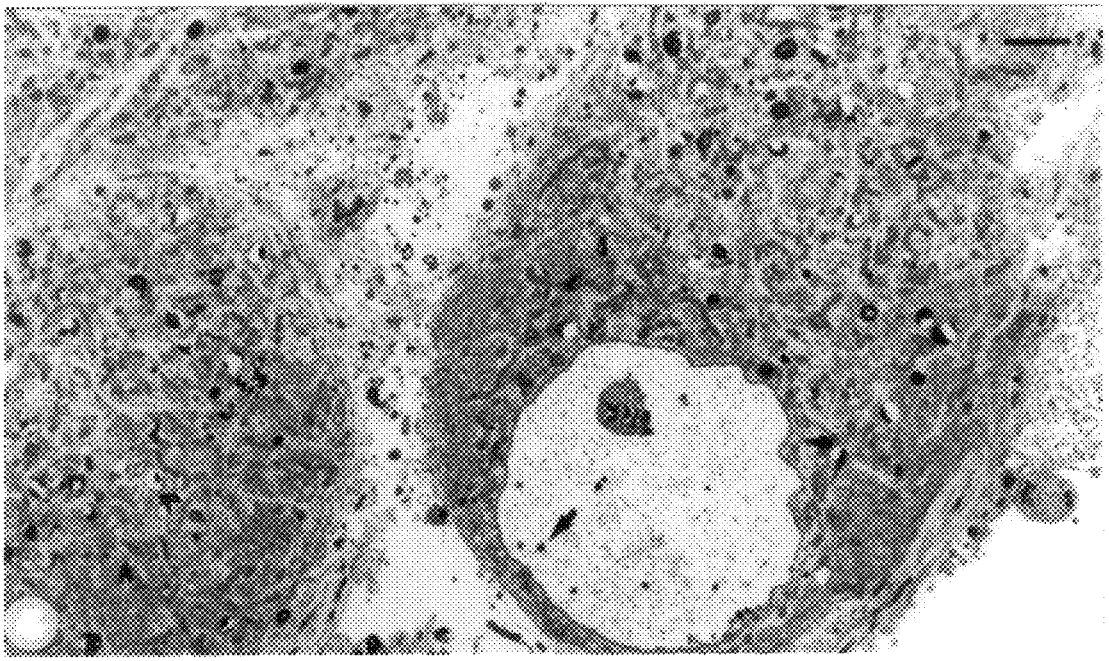
FIG. 4B shows the same type of neuron after infection with 10 MOI adenovirus. These cells contain small electron-dense inclusions in the nucleus (arrows; scale bar=0.5 $\mu$m but are otherwise indistinguishable from uninfected neurons.
Figure 4C:
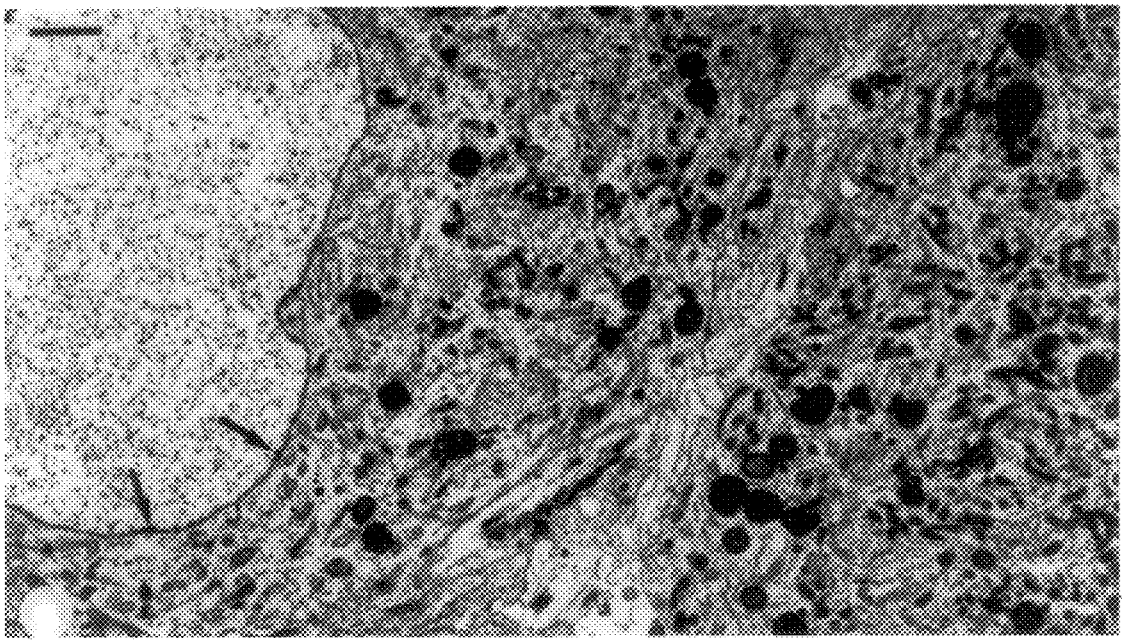
FIG. 4C shows the same type of neuron after infection at 50 MOI with an adenovirus vector. The cytoarchitecture is normal except for small, electron-dense nuclear inclusions (scale bar=0.4 $\mu$m).

Cells were first examined following infection at the lower range of 10 MOI, which results in the transduction of approximately 70% of cells. The ultrastructure of these cells in general was indistinguishable from non-infected cells (FIG. 4A); the cytoplasms appeared normal, with healthy intact organelles, and the nucleus contained normal chromatin (FIG. 4B). In some cells, very small electron dense inclusions were found in nuclei of otherwise healthy cells (FIG. 4B). At 50 MOI, cellular organelles remained intact, and the structure of the nucleus appeared normal, although slightly more nuclear inclusions were visible (FIG. 4C).

Figure 4D:
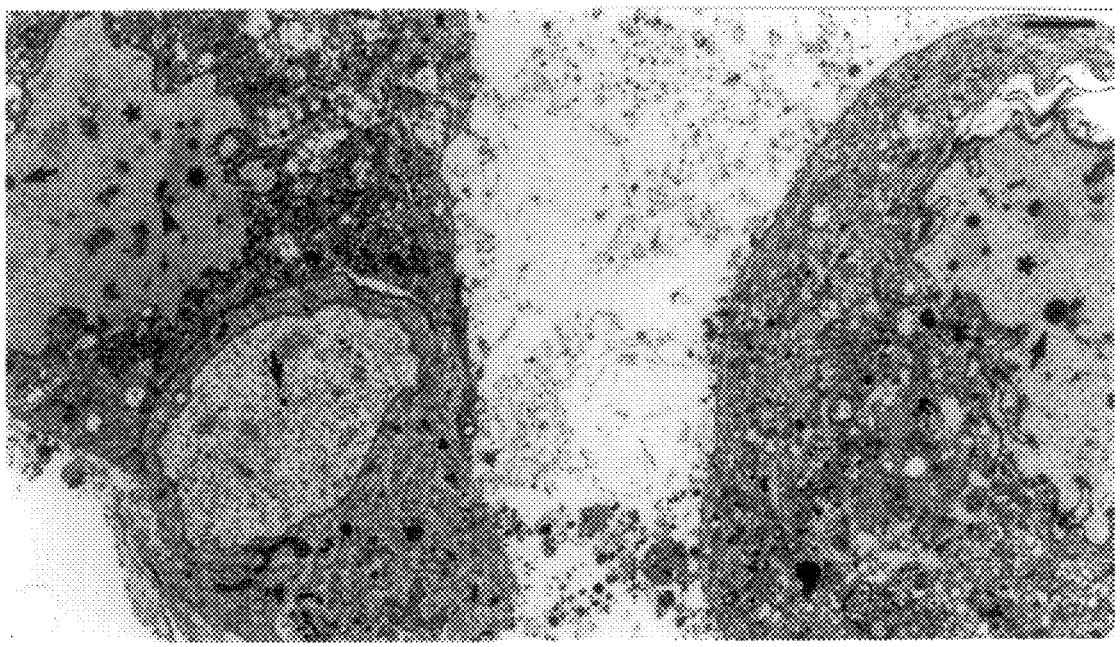
FIG. 4D shows the same type of neuron infected at 100 MOI with adenovirus. The cytoarchitecture is significantly deteriorated: chromatin disintegration (asterisks), very large electron-dense inclusions (arrow), and aggregates of filaments in nucleus are evident (arrowhead) (scale bar=0.7 $\mu$m.

At higher concentrations of adenovirus, where significant cytotoxicity was revealed by assays of mitochondrial function, nuclear abnormalities were readily apparent (FIG. 4D). These abnormalities included large electron dense inclusions and an accumulation of filamentous aggregates that are commonly found in neurons undergoing degeneration. At high titres, some neurons exhibited disintegration of chromatin (FIG. 4D). Ultrastructural examination revealed no features characteristic of apoptosis, even at highest titres examined (500 MOI) relative to uninfected controls. These results indicate that adenovirus can be used at titres which infect the majority of cells without provoking adverse cytological changes. Virus concentrations, however, should be carefully controlled as excessive infection rates result in deterioration of nuclear structure.

EXAMPLE V

ELECTROPHYSIOLOGICAL FUNCTION OF NEURONS INFECTED WITH RECOMBINANT ADENOVIRUSES

Although cells infected with 10 to 50 MOI of recombinant adenovirus were normal with respect to mitochondrial function and cytoarchitecture, neuronal function was characterized by examining the cell's electrophysiological properties.

Electrophysiology

Recombinant adenovirus-infected and control superior cervical ganglion (SCG) neurons were voltage-clamped using a whole-cell patch recording technique to measure outward potassium ($K^+$) currents (McFarlane et al., J. Neurosci. 13:2591–2600, 1993). Briefly, SCG neurons were harvested on the first postnatal day, cultured for 3 days, infected with Ad5CA17LacZ at an MOI of 50 for 24 hours, then cultured for an additional 7 days prior to electrophysiological recordings. The cells were fixed with 2% paraformaldehyde-0.2% gluteraldehyde immediately following recording and stained with X-gal to detect β-galactosidase activity. Only cells that exhibited β-galactosidase activity were considered to have been infected.

The total outward current in SCG neurons is made up of three voltage-gated currents which differ in their kinetic and voltage-dependent properties: a non-inactivating current (IK); a fast transient A-type current (IA) that inactivates with a time course of 10–30 ms; and a small slow transient A-type current (IAs) that inactivates with two components, one with a time constant of 100–300 ms, the second with a time constant of 1–3 ms (McFarlane, J. Neurophys. 67:1291–1300, 1992). By holding the membrane at different potentials it is possible to selectively activate one or two of the currents, and thus characterize individual currents by subtraction techniques. Briefly, the membrane was held at a potential of −10 or −20 mV where depolarizing steps evoked only IK. The IK currents were subtracted from total currents (IA+IK+IAs) evoked by steps to the same depolarizing potentials from a more negative potential, −90 mV, to isolate the A-currents. For measurement of the current density (pA/pF), IA and IK current amplitudes were determined from the current evoked by a voltage step to +30 mV after each current was isolated from the other two, and divided by the cell capacitance (pF). Cell capacitance was obtained by integrating the capacity current evoked by a 10 mV hyperpolarizing voltage step and then dividing this current by the voltage step.

Voltage steps were delivered by a computer-controlled stimulator. The software for stimulation, data acquisition, and analysis was written by Mr. A. Sherman (and is publically available through Alembic Inc., Montreal, Quebec. Membrane currents were filtered with a List EPC-7 amplifier, sampled at 5 kHz, displayed, and stored online. For all experiments, the voltage steps were 125 ms long.

All experiments were performed at room temperature (21–24° C.). The pipettes were filled with intracellular media (5 mM NaCl, 50 mM potassium acetate, 65 mM KF, 1 mM $MgCl_2$, 10 mM HEPES (pH 7.4, adjusted with KOH), 10 mM EGTA, 0.5 mM $CaCl_2$); the pipette current was balanced to zero with the pipette immersed in the bathing solution. The neurons were continuously superfused with extracellular solution (140 mM Choline Cl, 2 mM NaCI, 5.4 mM KCl, 0.4 mM $CaCl_2$, 0.18 mM $MgCl_2$, 10 mM HEPES (pH 7.4 adjusted with NaOH), 5.6 mM glucose, 0.5 mM tetrodotoxin (TTX), and 1.5 mM $CaCl_2$ (pH 7.3–7.4) at a rate of 0.5 ml/min, during the recording session. The extracellular solution included pharmacological agents to block inward sodium and calcium currents, and calcium-dependent currents as previously described (McFarlane, J. Neurophys. 67:1291–1300, 1992).

Figure 5A:
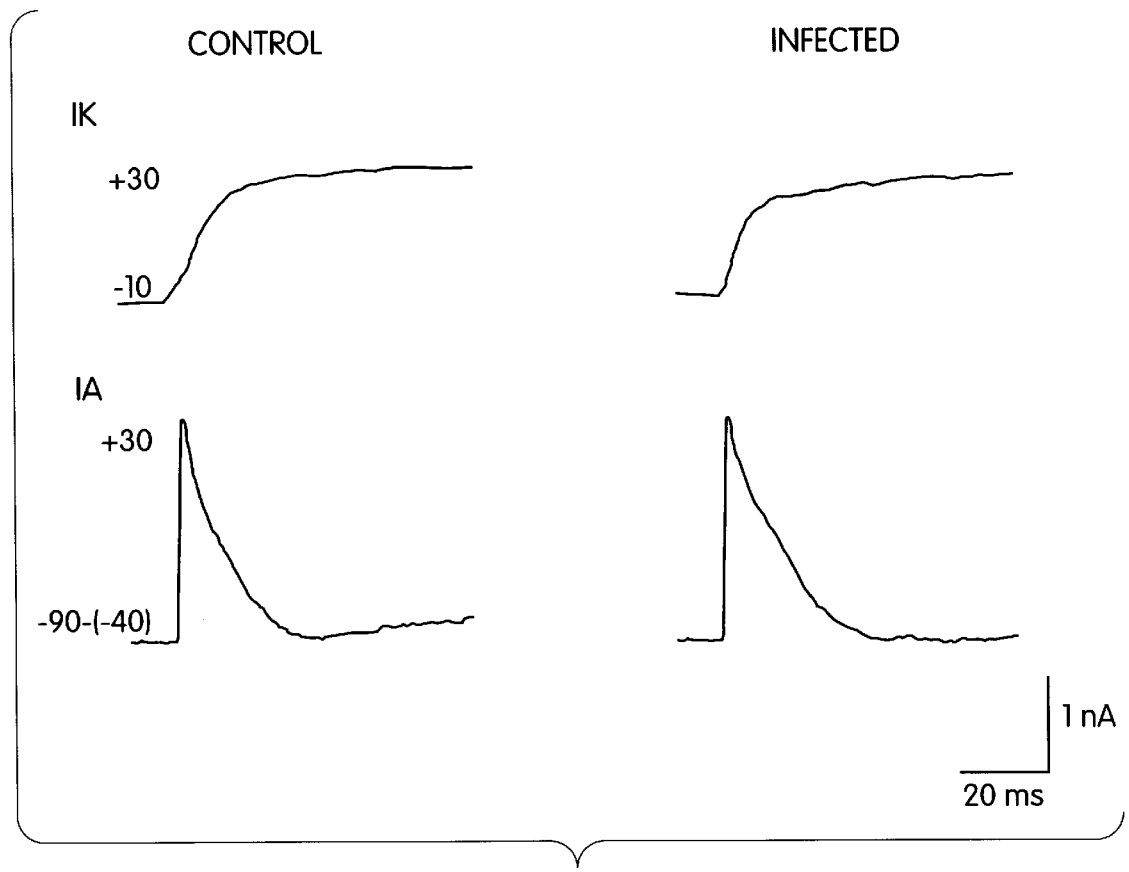
FIG. 5(A–B) are tracings representing voltage-gated potassium-currents on adenovirus-infected, β-galactosidase-expressing sympathetic neurons and uninfected neurons (FIG. 5A), and a pair of bar graphs representing the current densities in these cells. Depolarizing voltage steps from a Vh of −10 mV activate only a slowly activating, non-inactivating current (IK; shown in the uppermost tracings of FIG. 5A). IA (shown in the lower tracings) was isolated by subtracting currents from Vh of −40 mV (IK+IAs) from the corresponding currents evoked from a Vh of −90 mV (IK+IAs+IA).
In FIG. 5B, the average current densities (pA/pF), which were measured as the peak isolated potassium current (pA) divided by the membrane capacitance (pF) are shown for β-galactosidase-positive neurons (n=6); and uninfected control neurons.
Figure 5B:
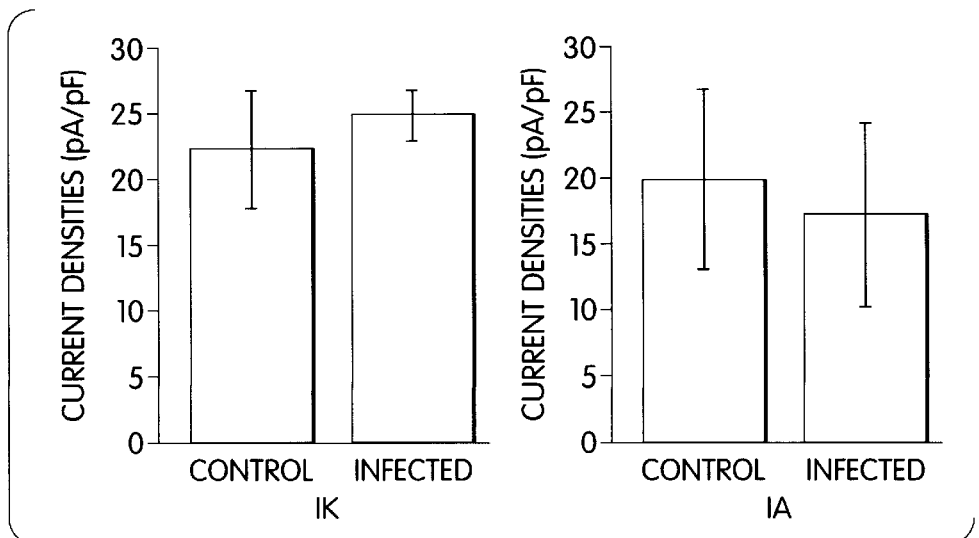

In sympathetic neurons expressing β-galactosidase seven days following infection, the current densities (pA/pF) for IK and IA were found to be similar to those previously reported for cultured SCG neurons (McFarlane et al., J. Neurosci. 13:2591–2600, 1993), and not significantly different from those of control, uninfected SCG neurons (FIGS. 5A and 5B). Neurons infected with up to 50 MOI of recombinant adenovirus, therefore, appear to function normally for at least 7 days.

EXAMPLE VI

OVEREXPRESSION OF P53 INDUCES APOPTOTIC CELL DEATH IN POSTMITOTIC NEURONS

The findings discussed above indicate that adenovirus vectors can be used to genetically alter primary neurons within controlled parameters. Therefore, this approach was used to determine whether overexpression of p53 was sufficient to induce programmed cell death in postmitotic neurons. A recombinant adenovirus, Adwtp53, which carries a wild-type p53 expression cassette on the same pJM17 vector backbone as the lacZ reporter gene, was used for these studies. Initially, to determine if adenovirus-mediated delivery of human wild-type p53 could lead to stable overexpression of p53 in cultured sympathetic neurons, cells were infected at 50 MOI with recombinant adenoviruses carrying either human p53 (Adwtp53) or lacZ (AdCA17LacZ), and immunostained with an antibody specific for human p53.

Immunofluorescence

For immunofluorescence detection of human p53 delivered by adenovirus vectors, specimens were fixed for 5 minutes in methanol:acetone (1:1) and allowed to air dry for 5 minutes. Following rehydration, cells were blocked in PBS containing 3% goat serum. A mouse monoclonal antibody that specifically binds an amino terminal epitope of human p53 (DO-1) (Santa Cruz Biotechnology) was used. The primary antibody was diluted in this same blocking solution (1:50) and incubated on coverslips overnight at 4° C. Following 3 washes in PBS, a goat anti-mouse secondary antibody conjugated with CY3 (Jackson Laboratories; diluted at 1:2000) was applied and incubated for 1 hour at 25° C. After 3 washes in PBS, coverslips were mounted in glycerol and examined with a Zeiss Axioskop microscope.

Figure 6A:
FIG. 6(A–B) are photographs which show that human p53 overexpression is localized to the nucleus of sympathetic neurons. Sympathetic neurons infected with a recombinant adenovirus encoding β-galactosidase, AdCA17lacZ, are shown in FIG. 6A and comparable cells expressing human wild-type p53, Adwtp53 are shown in FIG. 6B. Arrows point to pyknotic nuclei overexpressing human p53 (scale bar=20 $\mu$m).
Figure 6B:
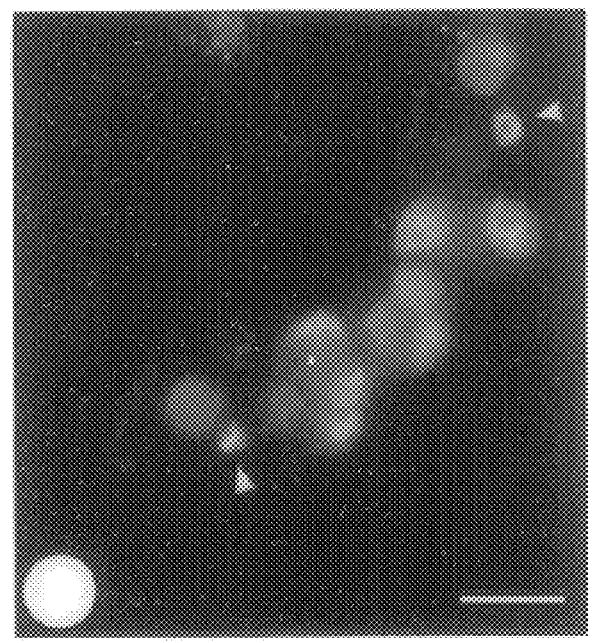

Neurons infected with AdCA17LacZ were not immunoreactive for human p53 (FIG. 6A), while those infected with Adwtp53 exhibited strong nuclear staining in over 80% of cells (FIG. 6B).

To more precisely determine the extent of p53 overexpression relative to endogenous levels, transduced sympathetic neurons were harvested at 30 and 48 hours following infection with 50 MOI of Ad5CA17LacZ or Adwtp53, and the levels of p53 protein were examined by Western blot analysis with an antibody that recognized both rodent and human p53.

Western Analysis

For the detection of p53 protein, cells were harvested in lysis buffer (Slack et al., J. Cell Biol. 129:779–788, 1995) 48 hours following infection with a titre of 50 MOI. Protein was separated on a 10% acrylamide gel and transferred to a nitrocellulose membrane. After blocking for 2 hours in 5% skim milk, the membrane was incubated in a solution containing Ab1, a mouse monoclonal antibody directed against murine and human p53 (1:10) (Oncogene Science, Cambridge, Mass.) overnight at 4° C. Following 5 washes in TBST (5 minutes each), filters were incubated for 1 hour at 25° C. in a goat anti-mouse secondary antibody conjugated to horseradish peroxidase. Filters were again washed 5 times in TBST for 5 minutes each wash. The Western blots were developed by the ECL chemiluminescence system™ (Amersham), according to the manufacturer's instructions.

Figure 7A:
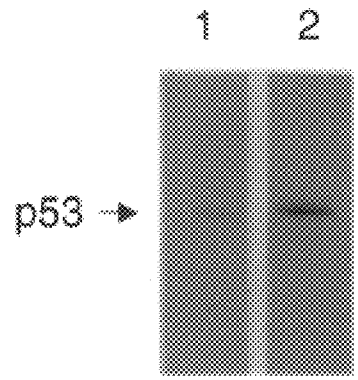
In FIG. 7A, Lane 1 contains protein harvested from uninfected neurons and Lane 2 contains protein harvested from Adwtp53-infected neurons, which express p53.
Figure 7B:
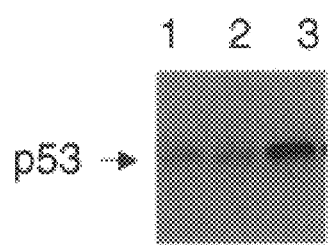
In FIG. 7B, Lane 1 contains protein harvested from uninfected neurons, Lane 2 contains protein harvested from neurons infected with 50 MOI pAdCA17lacZ, and Lane 3 contains protein harvested from neurons infected with 60 MOI Adwtp53.

These experiments demonstrated that endogenous p53 was stably expressed in sympathetic neurons, and that infection with Ad5CA17LacZ did not affect endogenous p53 expression (FIG. 7B). In contrast, by 30 hours following infection with Adwtp53, p53 protein was detectably overexpressed in sympathetic neurons (FIG. 7A), and by 48 hours, expression was much higher than endogenous levels (FIG. 7B). Coincident with this increased expression of p53 at 48 hours postinfection, morphological changes characterized by cell shrinkage became evident in cells infected with Adwtp53, while those carrying AdCA17LacZ appeared normal. Moreover, a noticeable number of dead and pyknotic p53-positive neurons were observed (FIG. 6B) relative to controls, suggesting that overexpression of p53 leads to neuronal death.

Figure 8A:
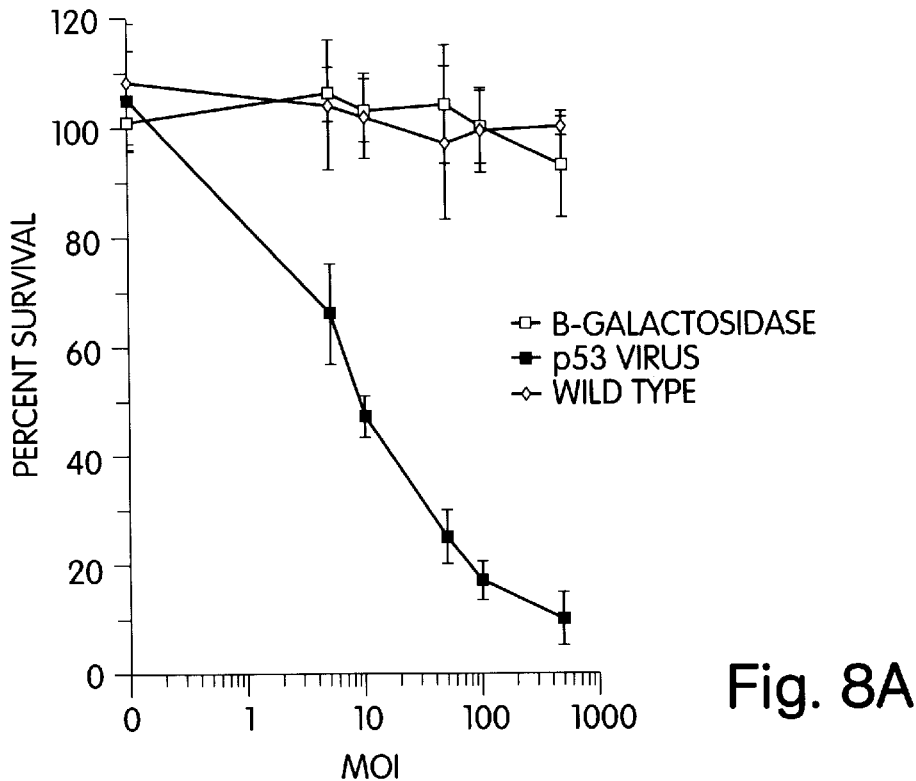
FIG. 8(A–B) are line graphs in which the percentage of surviving neurons is shown after infection at various MOIs (FIG. 8A), at various times (FIG. 8B) with wild-type adenovirus (○), recombinant adenovirus (Ad5CAI7LacZ; □), and a recombinant adenovirus carrying wild-type p53 (Adw4p53; ■).

To quantitate the extent of neuronal death following p53 overexpression, cell survival was measured with the metabolic assay described above, where the conversion of tetrazolium salt to formazan salt is measured using a cell titer 96 Assay kit™. Three days after plating sympathetic neurons were infected in parallel with Ad5CA17LacZ and Adwtp53 at titres ranging from 5 to 500 MOI. The cell survival assay of lacZ infected neurons revealed no changes in cell viability 72 hours following infection, even at the highest MOI of 500 (FIG. 8A). In contrast, cells infected with Adwtp53, under identical conditions, exhibited a 40% decrease in cell survival at 5 MOI, and a 65% decrease at 10 MOI (FIG. 8A). Higher levels of virus resulted in a dramatic 75 to 85% loss of cell viability by 72 hours. As an additional control experiment, sister cultures were infected with wild-type adenovirus at similar MOIs. Surprisingly, even wild-type adenovirus did not affect the survival of sympathetic neurons for up to 72 hours (FIG. 8A).

Figure 8B:
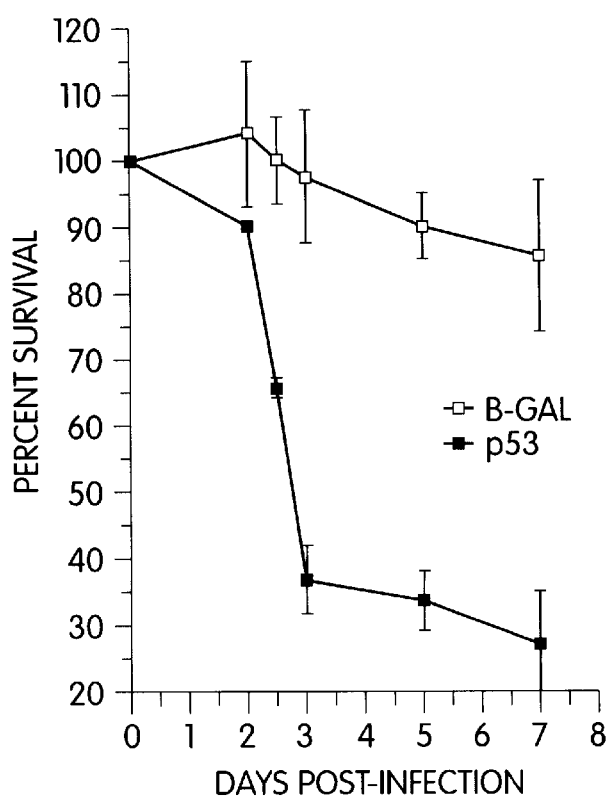

These data indicate that overexpression of human p53 leads to the death of sympathetic neurons. To ascertain the timecourse of neuronal cell death following p53 overexpression, parallel experiments were carried out with neurons infected at 50 MOI with Ad5CA17LacZ and Adwtp53. Survival was measured at 2, 2.5, 3, 5, 7, and 10 days following infection. Neuronal cell death was first detectable by 48 hours when a 10% decrease in cell survival was evident (FIG. 8B), while by 72 hours a dramatic 60% to 70% loss in cell viability was detected. Cell death then continued at a very low level for the remainder of the assay. Thus, cell death begins 48 hours following infection with Adwtp53, with the majority of neurons dying between 2 and 3 days.

To determine if p53-induced cell death was due to apoptosis, three different assays were conducted: (1) the isolation of nucleosomal DNA to visualize DNA ladders, (2) TUNEL staining to visualize apoptosis immunohistochemically, and (3) electron microscopy.

Isolation of Fragmented DNA

To examine DNA fragmentation, $10^6$ neurons were seeded on a 60 mm tissue culture dish under standard culture conditions. Cells were infected with recombinant adenovirus 3 days following plating, and were harvested 48 hours following infection. Cells were harvested, washed once with PBS, and used for DNA isolation as described previously (Slack et al., J. Cell Biol. 129:779–788, 1995). Lysis buffer 1.2 ml was added to 100 μl of cells suspended in TE (10 mM Tris-HCL, pH 8.0, and 1 mM EDTA). Lysis was allowed to proceed at room temperature for 15 minutes, after which time the lysate was centrifuged for 15 minutes at 12,000 rpm. The gelatinous pellet was removed with a pipet, and the supernatant was digested with 100 μg/ml RNase A at 37° C. for 30 minutes. The DNA was then precipitated by adding an equal volume of 100% ethanol and NaCl such that the final concentration was 0.5 M. Following centrifugation, the pellet was washed with 70% ethanol and resuspended in 50 μl of TE buffer. Fragmented DNA was end-labelled with [$^{32}$-P]-dCTP using Klenow (Promega) for 15 minutes at room temperature. DNA ladders were resolved by running end-labelled DNA on a 2% agarose gel using a 100 bp ladder as a standard.

TUNEL Staining

To assay apoptosis immunohistochemically, terminal transferase was used to visualize fragmented DNA (TUNEL staining). Parallel cultures were infected with Adwtp53 or pCA17lacZ at 50 MOI. After 72 hours, the cells were fixed with acetone:methanol (1:1) for 10 minutes at −20° C. Fifty microliters of a cocktail consisting of 1.0 gl Biotin dUTP (Boehringer Mannheim, Indianapolis, IN, Cat.#109307), 1.5 µl terminal transferase (Promega Cat. #M187/1), 20 µl of 5 X TdT buffer (Promega), and 78 µl distilled water was added to each coverslip. Following a 1 hour incubation at 37° C., coverslips were washed three times in PBS (pH 7.4), and once in Tris-buffered saline (pH 8.0) to stop the reaction. Coverslips were incubated with a streptavidin-tagged secondary antibody, CY3 (Jackson Laboratories, West Grove, Pa.) diluted at 1:2000 for 30 minutes. After three 5-minute washes in PBS, samples were mounted in glycerol and examined with a Zeiss Axioplan microscope.

Figure 7C:
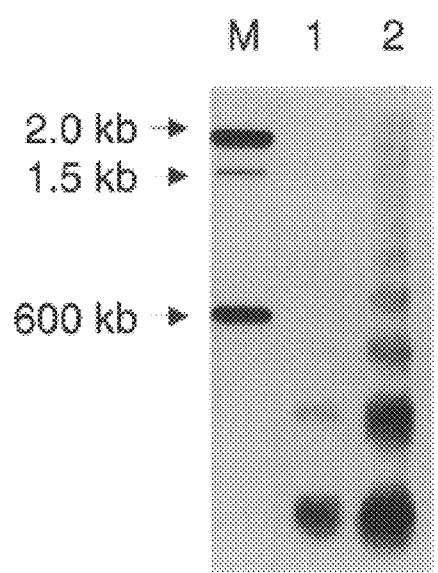
FIG. 7C is a photograph of a 2% agarose gel on which end-labelled DNA from neurons infected with 50 MOI of recombinant adenovirus AdCA17lacZ (lane 1), or with Adwtp53 (lane 2) was electrophoresed.
Figure 9A:
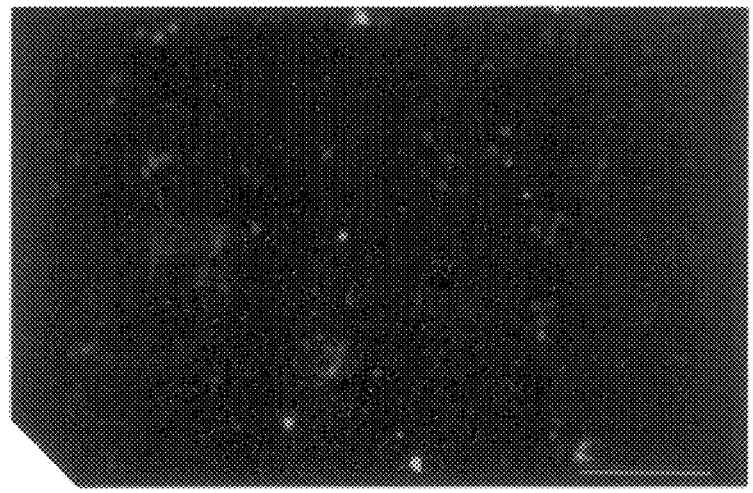
FIG. 9(A–F) are photographs of infected neurons following TUNEL staining. The cells shown in FIGS. 9A and 9B were photographed at low magnification (scale bar=400 nm) to show a representative view of the cell populations expressing lacZ (9A) and p53 (9B). At higher magnification, and viewed with phase contrast microscopy, degeneration of neuritic processes is shown in cells infected with Adwtp53 (9E) relative to cells infected with Ad5CA17lacZ (9C). The corresponding TUNEL staining shows pyknotic nuclei, which indicate apoptosis, in cells infected with Adwtp53 (9F).
Figure 9B:
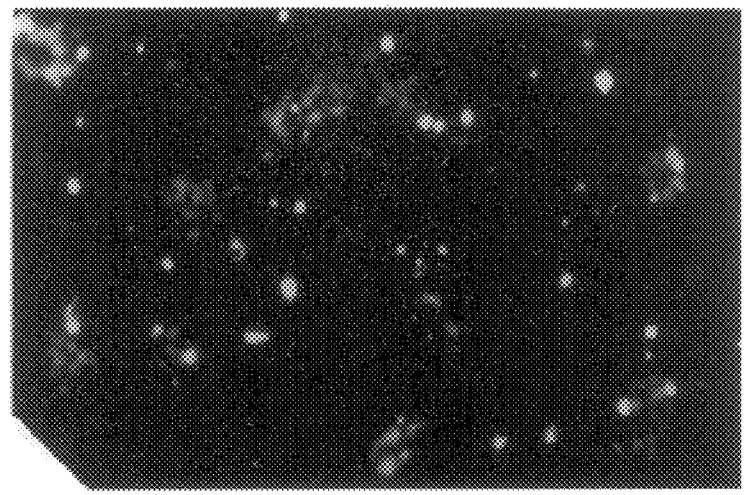
Figure 9C:
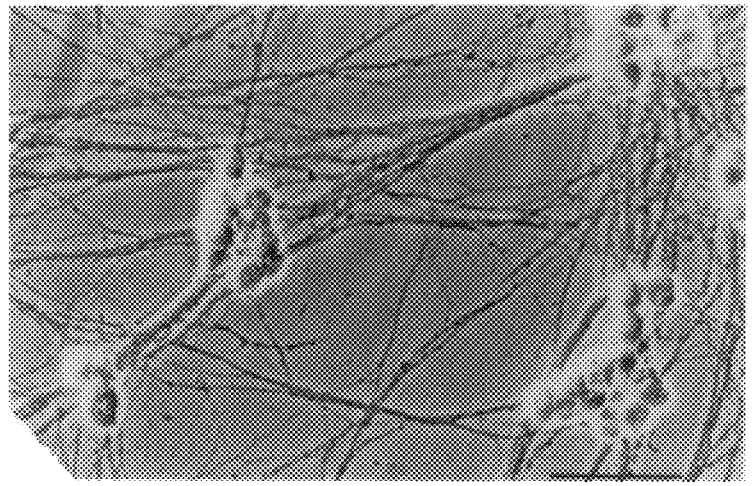
Figure 9D:
Figure 9E:
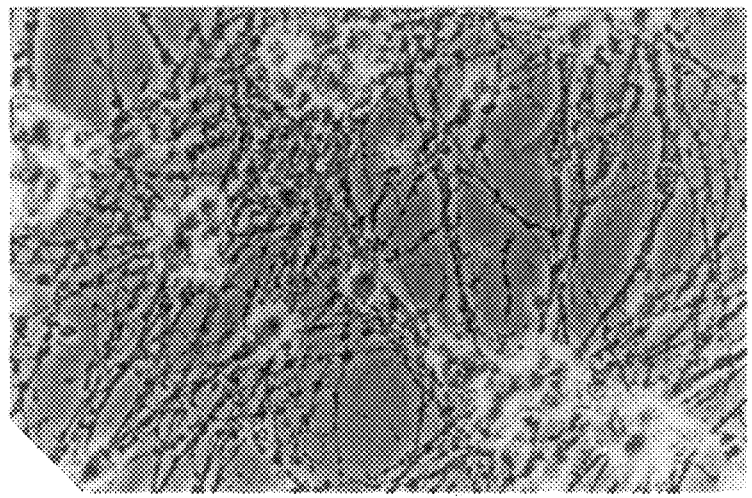
Figure 9F:
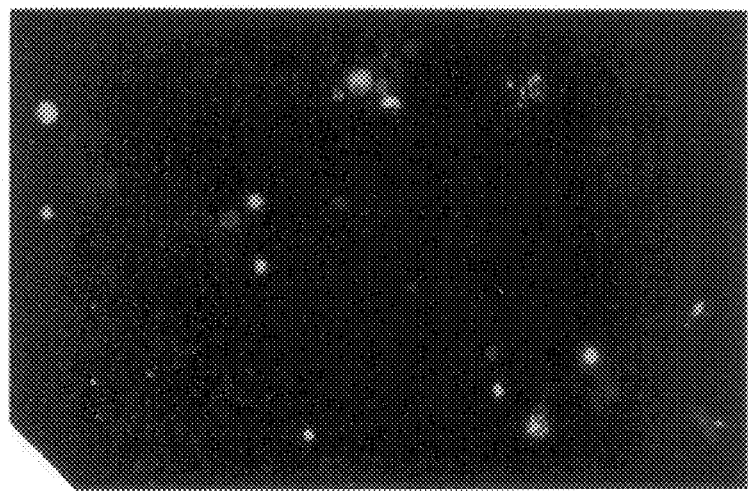

All three of these assays, which were conducted in parallel with cultures infected at 50 MOI with AdCA17LacZ or Adwtp53, indicated that overexpression of p53 leads to neuronal apoptosis. First, neurons infected for 48 hours with Adwtp53 showed significantly more DNA fragmentation than those infected with AdCA17LacZ (FIG. 7C), as demonstrated by DNA gel electrophoresis. Second, TUNEL staining revealed significantly higher levels of apoptosis in neurons overexpressing p53 relative to controls at 72 hours postinfection (FIGS. 9A and 9B). In Adwtp53-infected cultures, there were many pyknotic, TUNEL-positive nuclei (FIG. 9F), while only the occasional TUNEL-positive nucleus was observed in cultures infected with AdCA17LacZ (FIG. 9A and 9D). Coincident with this increase in TUNEL-labelling, p53-overexpressing neurons displayed dramatic neuritic degeneration (FIG. 9E), while those expressing β-galactosidase displayed normal morphology (FIG. 9C). Finally, analysis of these cultures by electron microscopy demonstrated enhanced apoptosis of sympathetic neurons infected with 50 MOI Adwtp53, as indicated by the collapse and condensation of the nuclear chromatin. In contrast, sympathetic neurons infected with AdCA17LacZ did not display enhanced apoptosis relative to uninfected controls, even at 500 MOI, at least as measured ultrastructurally. Thus, adenovirus-mediated overexpression of p53 is sufficient to cause the apoptotic death of postmitotic sympathetic neurons.

EXAMPLE VII

MODULATION OF APOPTOTIC CELL DEATH BY INFECTION OF POSTMITOTIC NEURONS WITH RECOMBINANT ADENOVIRUSES

Figure 10:
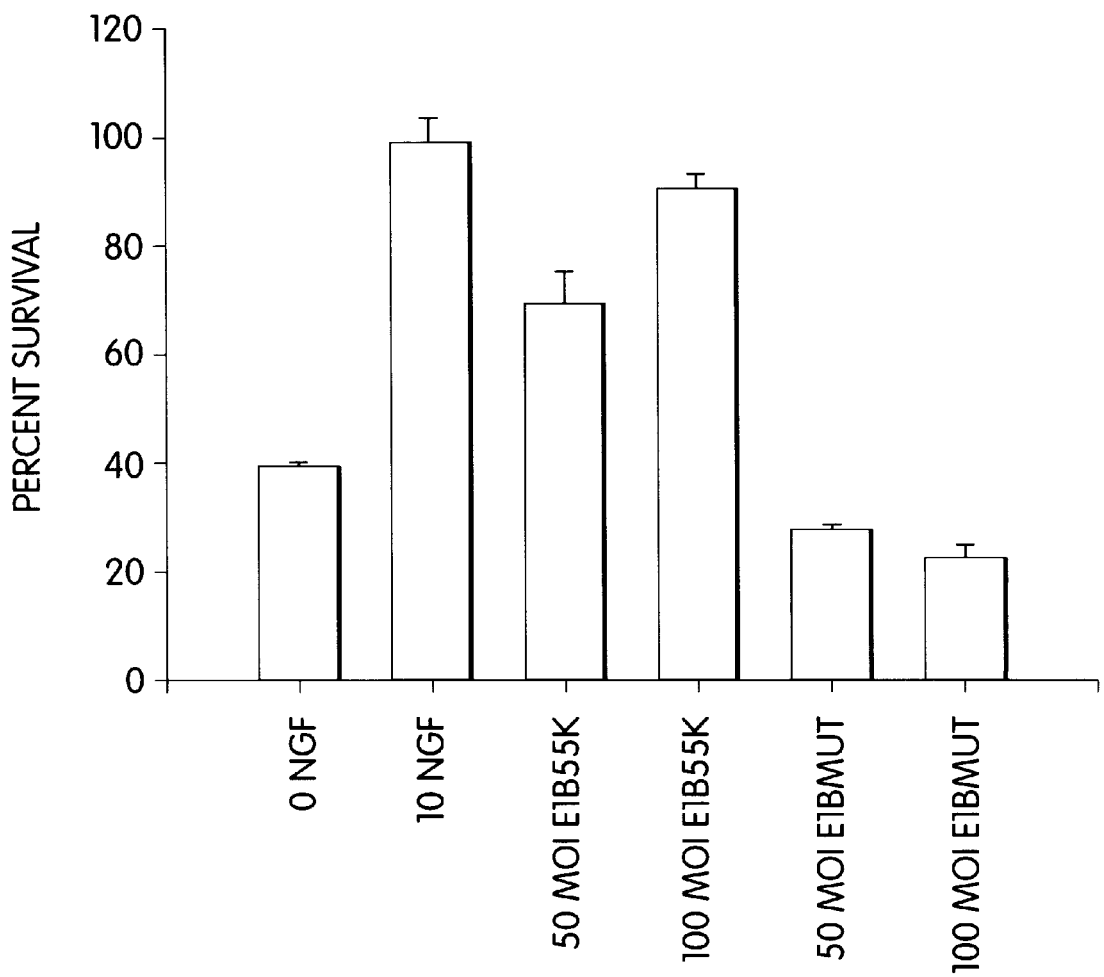
FIG. 10 is a graph showing that recombinant adenoviruses expressing the p53 inhibitor, E1B55K, rescue postmitotic sympathetic neurons from NGF withdrawal-induced death.

Inhibition of p53-Mediated Cell Death by a Recombinant Adenovirus Expressing E1B55K The experiments outlined above show that postmitotic neurons are induced to undergo apoptotic cell death upon infection of a p53-encoding retrovirus. Conversely, survival of postmitotic neurons is enhanced by infecting them with recombinant retroviruses encoding proteins that inhibit cell death. The graph shown in FIG. 10 shows that recombinant adenoviruses expressing the p53 inhibitor, E1B55K, rescue neurons from NGF withdrawal-induced death. Sympathetic neurons from P1 rat superior cervical ganglia (SCG) were cultured for 5 days in 50 ng/ml NGF, after which they were infected with an MOI of 50 or 100 of recombinant adenovirus expressing E1B55K, or mutant E1B55K which is unable to bind p53. Infections were performed in the presence of 50 ng/ml NGF. Two days post-infection, the cells were washed free of NGF and two days later survival levels were determined using MTT assays.

p53- and MEKK1-induced Cell Death is Inhibited by Injection of Postmitotic Neurons with Recombinant Adenoviruses Expressing Bcl-2 and Bcl-xL.

Figure 11:
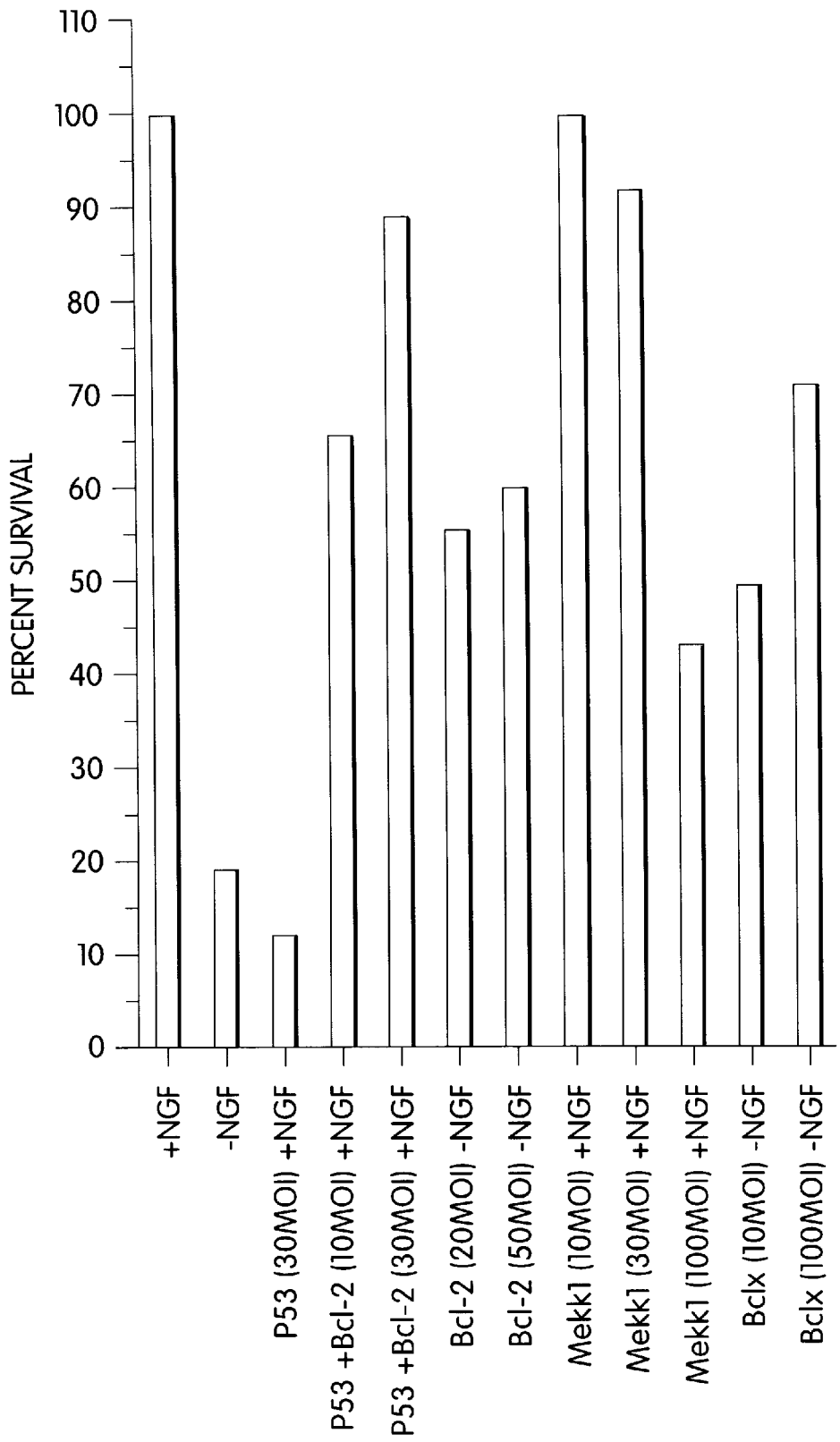
FIG. 11 is a graph showing that recombinant adenoviruses expressing p53 and MEKK1 kill postmitotic sympathetic neurons in the presence of NGF, whereas recombinant adenoviruses expressing the anti-apoptotic proteins Bcl-2 and Bcl-xL rescue neurons from NGF withdrawal-induced death.

The experiment shown in FIG. 11 demonstrates that recombinant adenoviruses expressing p53 or MEKK1 (a member of the mitogen-activated kinase cascade) kill neurons in the presence of NGF, whereas recombinant adenovirus expressing the anti-apoptotic proteins Bcl-2 and Bcl-xL rescue neurons from NGF withdrawal-induced death. Sympathetic neurons from P1 rat superior cervical ganglia (SCG) were cultured for 5 days in 50 ng/ml NGF, after which they were infected with an MOI of 10 to 100 of recombinant adenovirus expressing p53, MEKK1, Bcl-2, and Bcl-xL. Infections were performed in the presence of 50 ng/ml NGF. Two days post-infection, the cells were washed free of NGF and two days later survival levels were determined using MTT assays.

Nerve-Growth Factor (NGF)-Induced Cell Death is Inhibited by Injection of Postmitotic Neurons with a Recombinant Retrovirus Expressing the Docking Protein Gab1.

Figure 12:
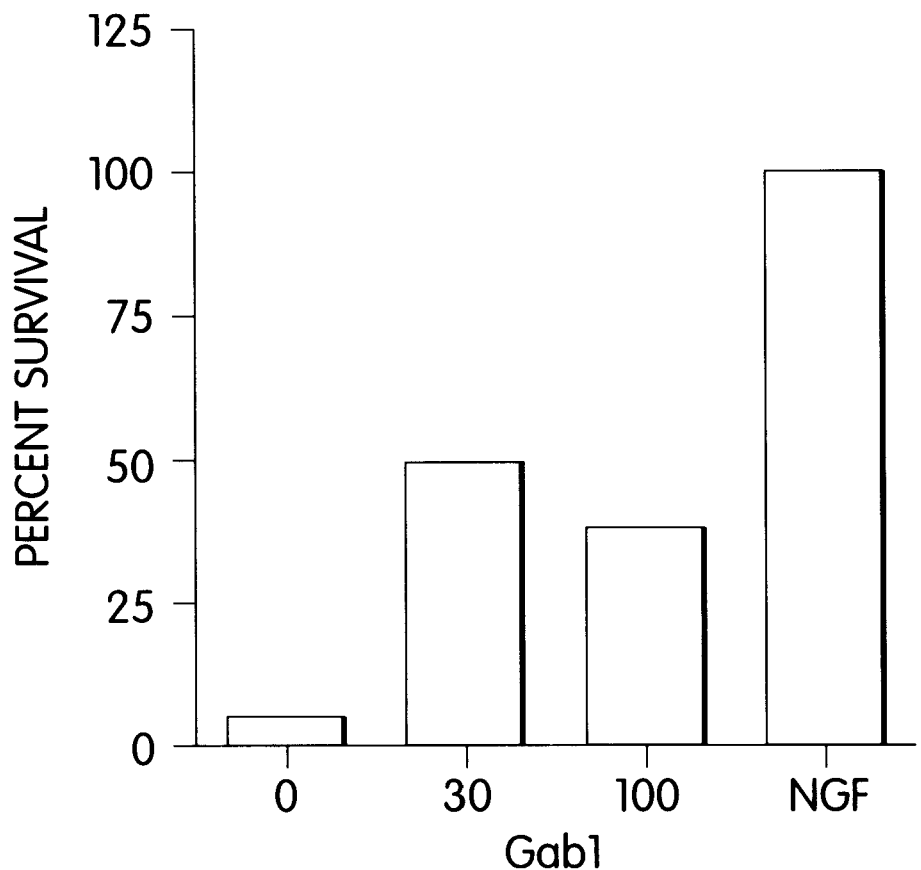
FIG. 12 is a graph showing that a recombinant adenovirus expressing Gab1 mediates survival of postmitotic sympathetic neurons.

The experiment shown in FIG. 12 demonstrates that Gab1 adenovirus mediates sympathetic neuron survival. Sympathetic neurons (10,000 neurons per assay point) were isolated at birth (P0) and were grown for 4 days in 10 ng/ml NGF. Neurons were washed free of NGF at day 4, and infected with recombinant adenovirus encoding Gab 1 at an moi of 30 or 100. The experiment shown in FIG. 12 demonstrates that per cent survival after five days of infection is relative to survival in 10 ng/ml NGF.

Figure 13:
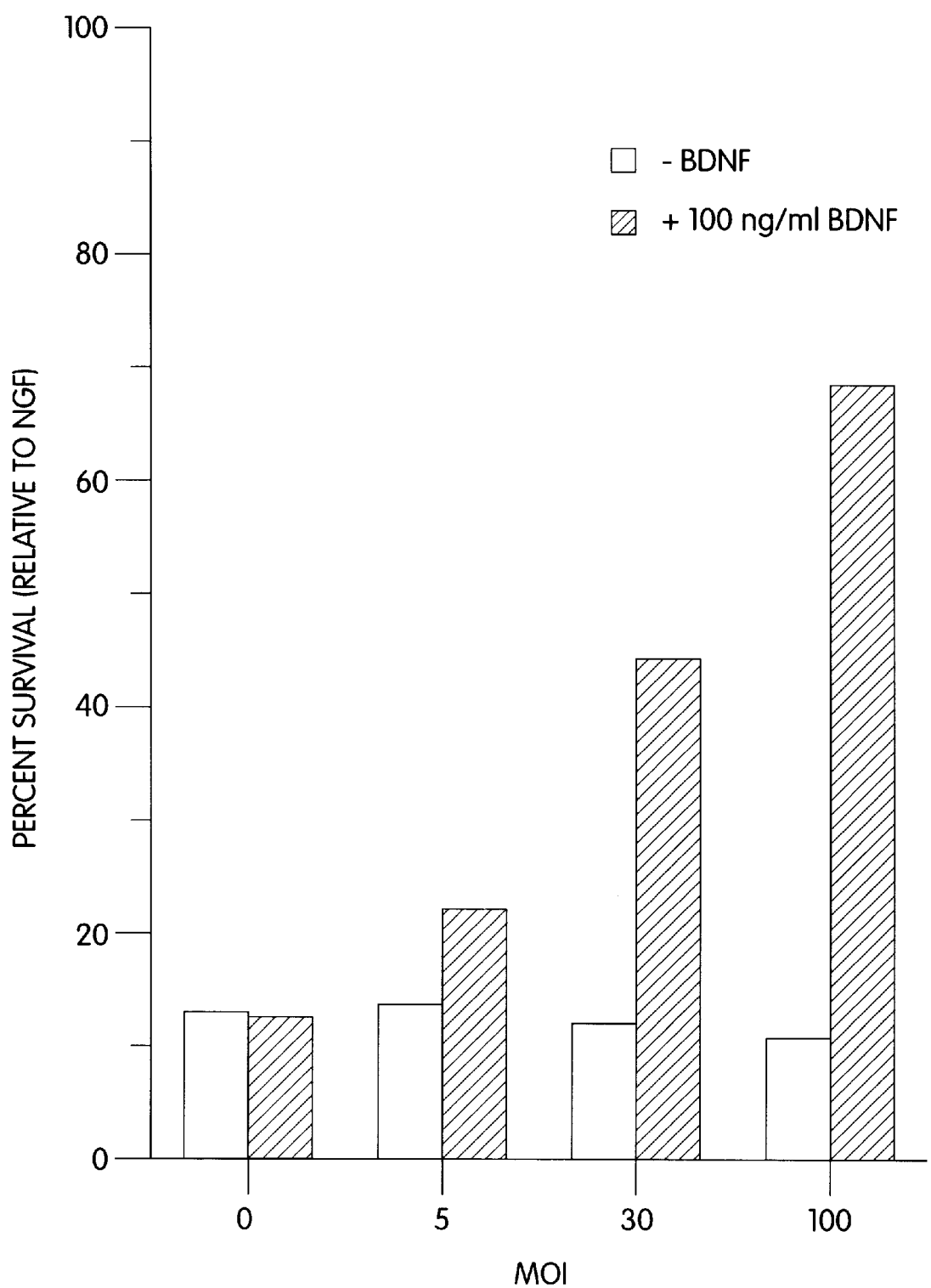
FIG. 13 is a graph showing that post-mitotic injection of a recombinant adenovirus expressing TrkB mediates sympathetic neuron survival.

Inhibition of Neuronal Cell Death by Recombinant Adenovirus Encoding Growth Factor Receptors The experiment shown in FIG. 13 demonstrates that TrkB adenovirus mediates sympathetic neuron survival. Sympathetic neurons which express TrkA but not TrkB (10,000 neurons per assay point) were isolated at birth (P0) and were grown for 4 days in 10 ng/ml NGF. Neurons were washed free of NGF at day 4, and infected in the presence of BDNF with recombinant adenoviruses encoding wild-type TrkB. The graph shows percent survival after five days in BDNF (hatched bars) or in the absence of BDNF (black bars) relative to survival in NGF.

Figure 14:
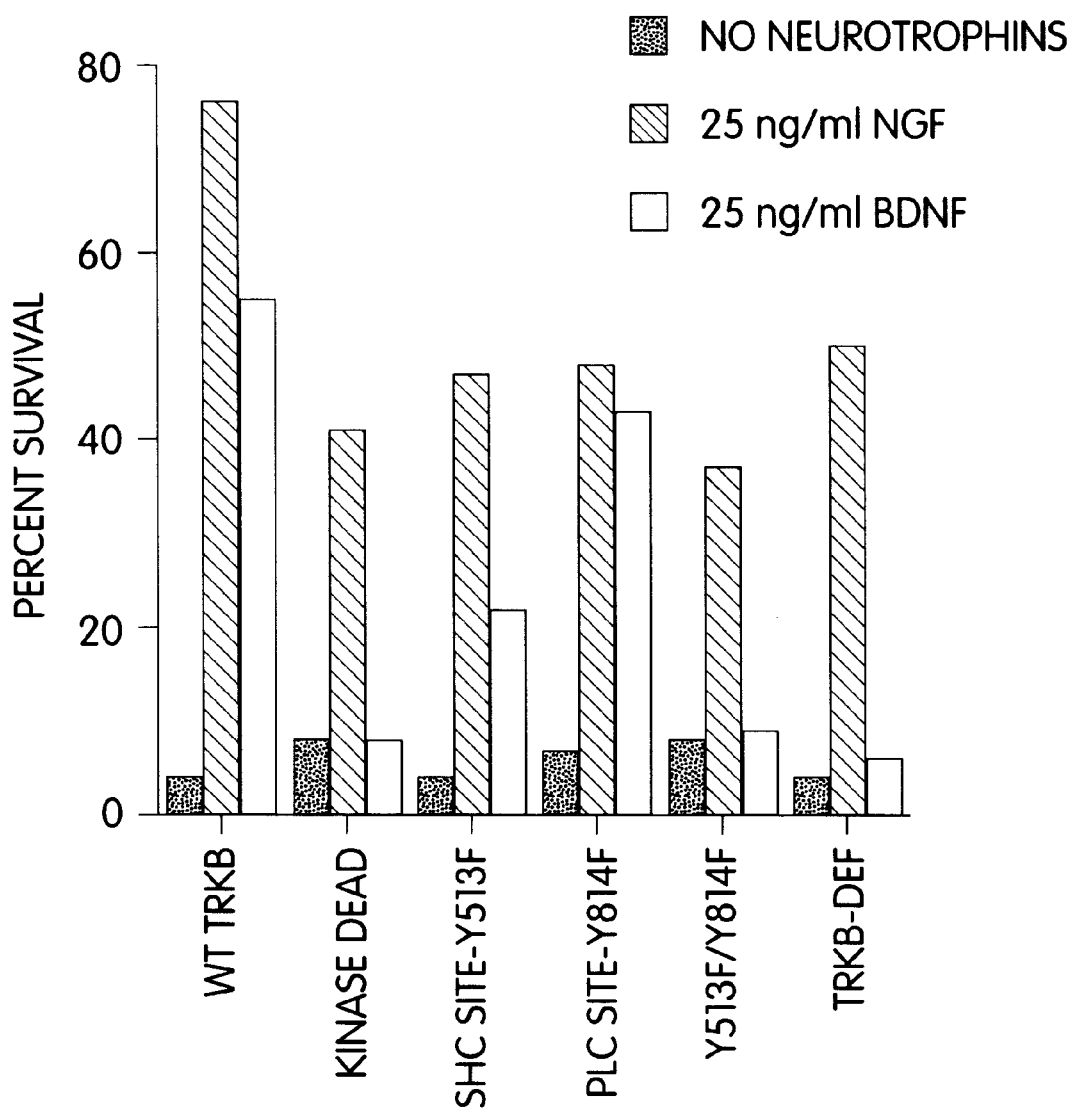
FIG. 14 is a graph showing that induction of neuron survival by adenovirus-encoded TrkB requires both the Shc/Ras/PI-3 kinase activation sites and the phospholipase C (PLC)-gammal activation sites of TrkB.
Figure 15A:
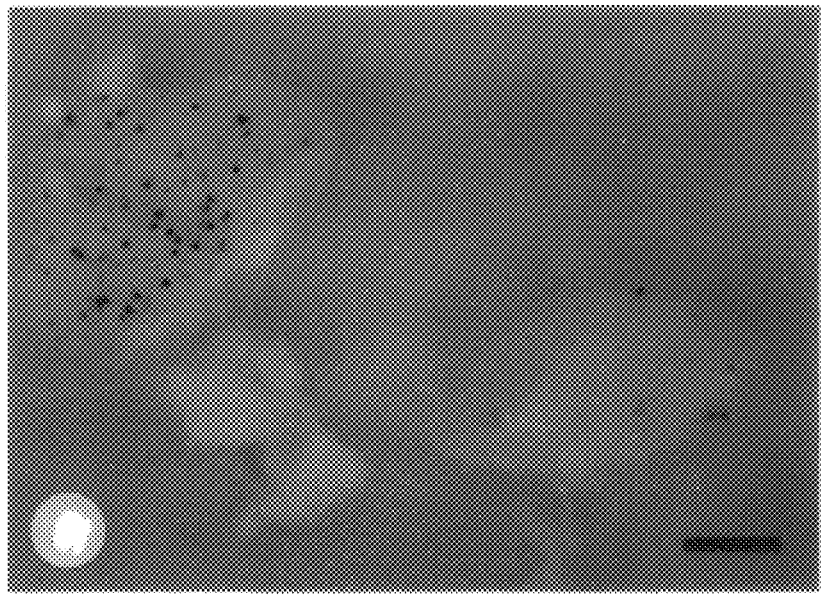
In FIG. 15A two superior cervical ganglia are shown; the ganglion on the left-hand side was harvested following adenovirus injection on that same side (i.e., the ipsilateral side), and the ganglion on the right-hand side was harvested from the contralateral, uninjected side of the same animal.
Figure 15B:
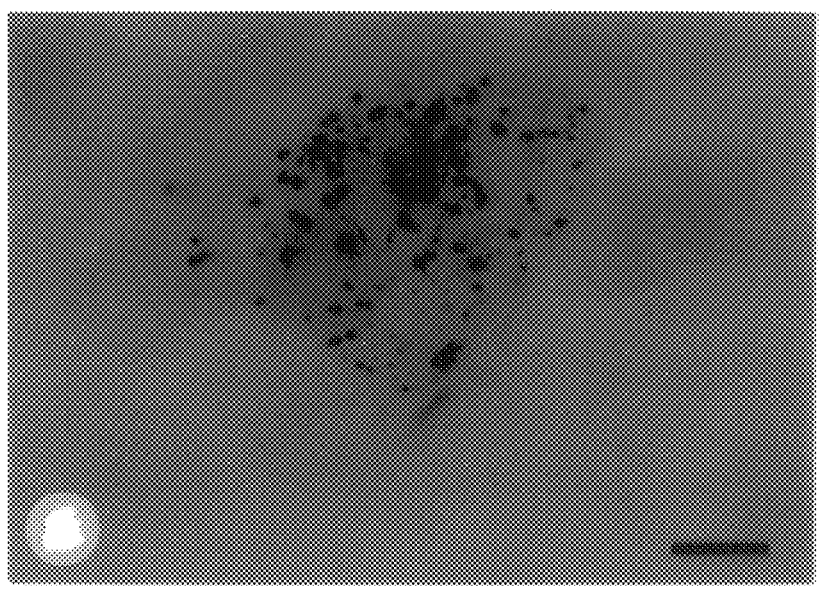
In FIG. 15B, the ganglion on the left-hand side of FIG. 15A is shown at higher magnification. Scale bar in FIG. 15A=300 $\mu$m; scale bar in FIG. 15B=240 $\mu$m.

The experiment shown in FIG. 14 demonstrates that TrkB mediated-sympathetic neuron survival requires both the Shc/Ras/PI-3 kinase activation sites and the phospholipase C (PLC)-gammal activation sites on TrkB. Sympathetic neurons (10,000 neurons per assay point) isolated at birth (P0) were grown for 4 days in 10 ng/ml NGF. Neurons were washed free of NGF at day 4, and infected in the presence of BDNF or NGF with recombinant adenoviruses encoding wild-type TrkB or TrkB containing mutations at sites that we have found to be required for the interactions of TrkA with intracellular signalling proteins. The TrkB proteins assayed were wild-type (WT) TrkB or the following TrkB mutations: kinase inactive; Y513F mutant defective in activation of SHC, Ras, and PI-3 kinase; Y814F defective in activation of phospholipase C (PLC)-gammal; Y513F/Y8 14F double mutant; or Def, defective in activating SHC, Ras, PI-3 kinase, phopholipase C (PLC)-gammal, and SNT. Sympathetic neuron survival was assessed at day 9 by MTT assay. The graph shows per cent survival after five days in BDNF (hatched bars) or in the absence of BDNF (dot bars), relative to survival in NGF (black bars).

EXAMPLE VIII

GENE TRANSFER TO SYMPATHETIC NEURONS IN VIVO

Because adenovirus appears to be an effective gene transfer vector in vitro, we set out to determine if the recombinant virus could be effectively delivered to SCG neurons in vivo. For in vivo administration, $5 \times 10^9$ pfu/ml were injected into the pinna of the ear of adult mice; the pinna is one of the targets of the axon terminals that extend from SCG neurons. Thirty minutes prior to injection of recombinant adenovirus, mice were injected with 0.05 mg/kg Buprenorphine (Temgesic™, Pickitt and Colman Ltd) as an analgesic and then anaesthetized by inhalation of Methoxyflurane (Metofane™, Janssen Pharmaceuticals). Fourteen days after administration of the adenovirus, mice were sacrificed by deep anaesthesia consisting of 100 mg/kg sodium pentobarbital (Somnitol™, MTC Pharmaceuticals, cambridge, Ontario). The superior cervical ganglia (SCG) were removed and rinsed in a solution containing 0.1 M $NaH_2PO_2$ (pH 7.3), 2 mM $MgCl_2$, 0.01% sodium deoxycholate, and 0.02% NP-40. The β-galactosidase gene product was visualized by incubating the ganglia at 37° C. in the same rinse solution containing 1 mg/ml X-gal, 5 mM $K_3Fe(CN)_6$, and 5 mM $K_4Fe(CN)_6$ for 3 hours. Ganglia were then rinsed 3 times, immersed in fixative (4% paraformaldehyde) for 1 hour, and examined microscopically. For histological examination, ganglia were cryoprotected by passage through solutions containing ascending concentrations of sucrose (12%, 16%, 18%) for at least 4 hours each, frozen, and sectioned at 15 μm. Sections were stained with eosin, dehydrated in ascending concentrations of ethanol followed by xylene, and coverslipped.

Numerous LacZ positive cells were seen in the ipsilateral SCG of the injected animals, indicating that adenovirus can be delivered to SCG neurons through retrograde transport. No staining was found in 2 of 3 animals in the contralateral ganglia, although 1 animal exhibited a few positive cells. Gross examination of the animals failed to reveal potential side effects such as inflammation or SCG dysfunction, which would have presented as redness of the ear or ptosis of the eye. No swelling was observed in ganglia containing transduced neurons during surgical removal.

It will be apparent to skilled artisans that comparable adenovirus vectors can be administered to other animals and to human patients in the same manner, i.e. via application to the target of the neurons which are meant to be transduced. It is well within the abilities of skilled artisans to carry out this administration. The adenovirus vector may be prepared as described herein and administered intravenously, intraarterially, subcutaneously, intrathecally, intraperitoneally, intramuscularly, intracerebrally, or intraventricularly. The route of administration and the effective dosage will depend on other parameter routinely assessed by practicing clinicians, including the age and general health of the patient, and other medications being concurrently administered.

EXAMPLE IX

INFECTION OF CORTICAL PROGENITOR CELLS AND POSTMITOTIC CORTICAL NEURONS WITH RECOMBINANT ADENOVIRUSES

The following experiments demonstrate that recombinant adenoviruses may be used to infect and modulate apoptosis in cortical progenitor cells and postmitotic neurons.

Cell Culture

The preparation of cortical progenitors from mouse embryos was based upon the method described by Ghosh et al. (1995) for rat cultures, and modified corresponding to Brewer et al., Nature 363:265–266, 1993. Cortices were collected from E12–13 mouse embryos, triturated and plated at a density of $10^5$ cells per well of a 4 well tissue culture plate. The culture medium consisted of Neurobasal medium (Gibco/BRL), 0.5 mM glutamine, penicillin-streptomycin, 1% N2 supplement (Gibco/BRL) and bFGF (40 ng/ml; Collaborative Research Inc.). After 48 hours medium was replaced with the same medium except 1% N2 supplement was now replaced with 2% B27 (Gibco/BRL). The cortical neurons generated from these progenitor cells could be maintained for at least 3 weeks under these conditions. For neurite extension assays, after 5 days the neurons were switched into medium containing 10 ng/ml nerve growth factor (NGF). When cells were cultured from transgenic mice, tissue from each embryo was removed, triturated and plated separately prior to genotyping. Mature postmitotic neurons were prepared from E17–18 embryos, from which cortices were collected, triturated in culture media (Neurobasal with 0.5 mM glutamine, penicillin-streptomycin, 0.5% N2, 1% B27 supplements), and plated at a density of $0.5 \times 10^6$ cells/ml.

Infection of Cortical Neurons with Recombinant Adenoviruses

Cortical progenitor cells were infected at the time of plating and cortical neurons were infected 8 days following plating to ensure that the vast majority of neurons in the cultures were postmitotic. For virus infection, cells were plated in 4-well tissue culture dishes in 400 μl medium with the addition of another 400 μl of medium containing the appropriate titre of vector. Eighteen hours following infection a complete medium change was carried out. The multiplicity of infection (5–100 MOI) indicates the number of plaque forming units added per cell. Cell survival assays were carried out after 72 hours post-infection with cortical progenitor cells and 4 days post-infection for cortical neurons.

Figure 17A:
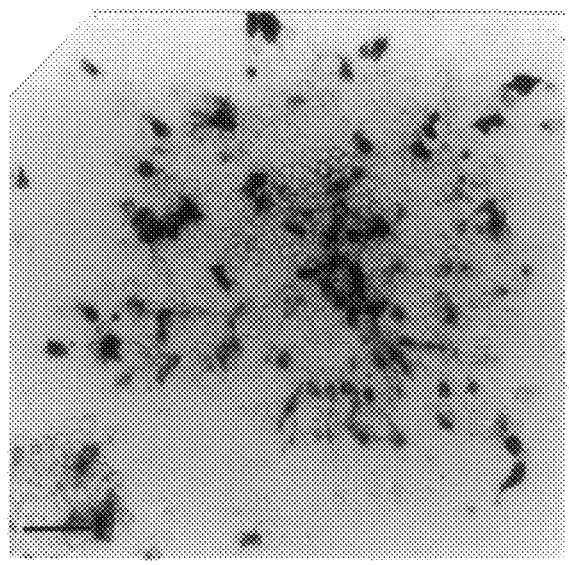
FIGS. 17(A–C) show that cortical progenitor cells and postmitotic cortical neurons efficiently express recombinant adenovirus-encoded proteins. Cortical progenitor cells (A) and postmitotic neurons (B) infected with AdlacZ and stained with X-gal. (C) Western blot of cortical progenitor cells infected with a recombinant adenovirus encoding El A.
Figure 17B:
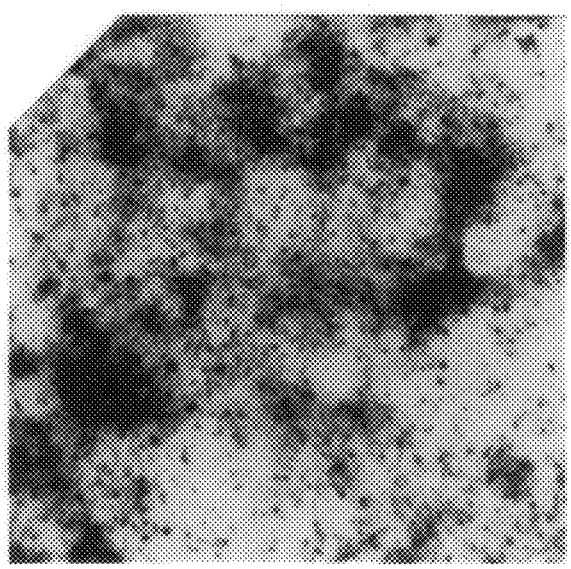
Figure 17C:
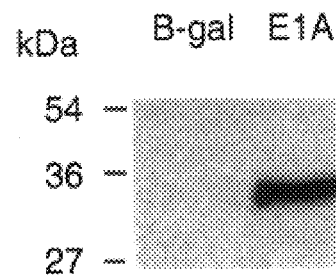

The experiments shown in FIGS. 17A and 17B demonstrate that infection of cortical progenitor cells and postmitotic cortical neurons with recombinant adenoviruses encoding lacZ (AdlacZ) or mutant E1 A (Ad1101) results in the efficient expression of adenovirus-encoded proteins. At 0 and 8 days in vitro, respectively, cortical progenitor cells (FIG. 17A) and neurons (FIG. 17B) were infected with recombinant AdlacZ at 25 MOI. After 48 hours cells were stained with X-gal to visualize β-galactosidase gene expression. In FIG. 17C cortical progenitors were infected with Ad1101 at 100 MOI upon plating, and protein was extracted 48 hours later. E1A 1101 was detected by Western blotting with M73 antibody. Scale bar=50 μm.

The experiments shown in FIGS. 18–21 demonstrate that cortical progenitor cells, but not postmitotic cortical neurons, are induced to die by E1A encoded by a recombinant adenovirus.

Figure 18A:
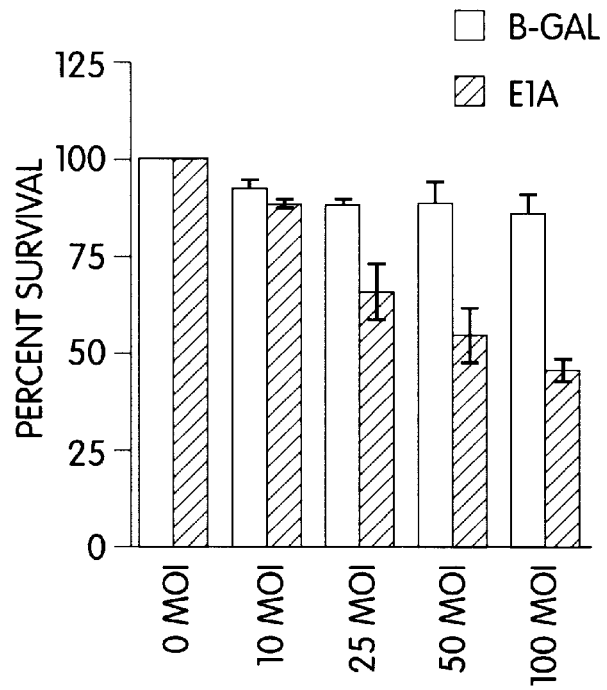
FIGS. 18(A–B) are graphs showing the survival of cortical progenitor cells (A) and postmitotic neurons (B) infected with lacZ-encoding (AdlacZ) and E1A-encoding (Ad1101) recombinant adenoviruses. Survival was measured by MTT assay.
Figure 18B:
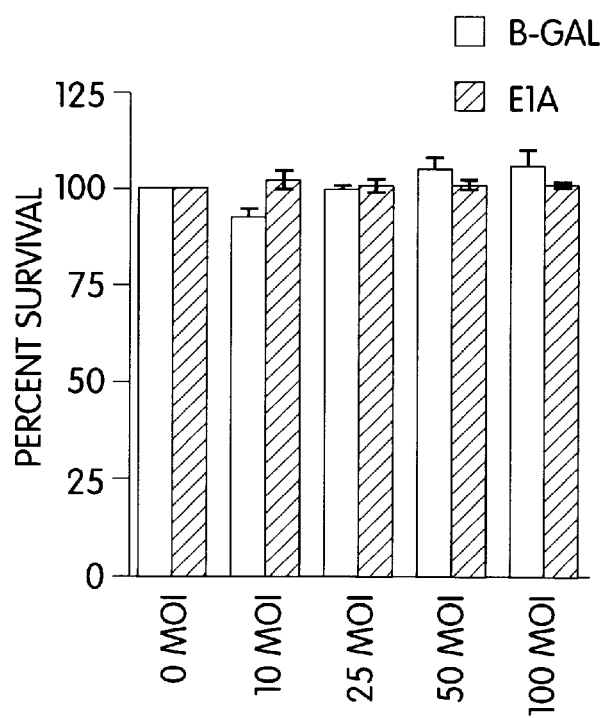
Figure 19A:
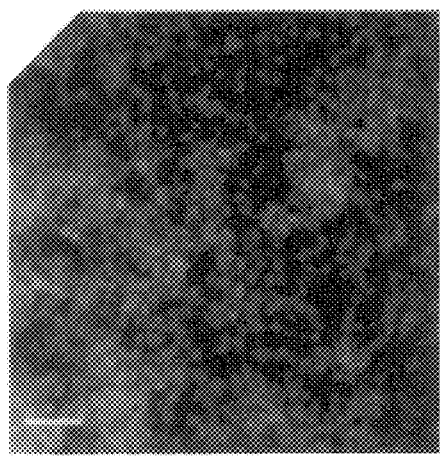
FIGS. 19(A–L) are photomicrographs showing a comparison of cell viability of cortical progenitor cells and postmitotic neurons infected with recombinant AdlacZ and Ad1101.
Figure 19B:
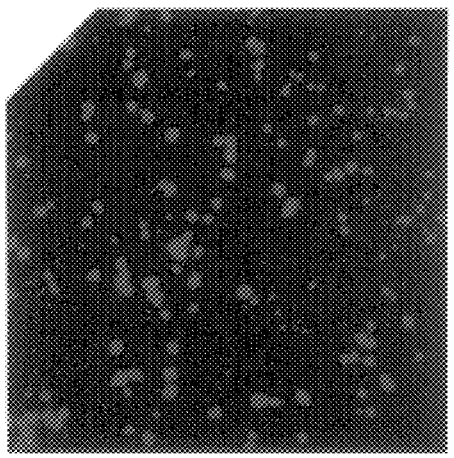
Figure 19C:
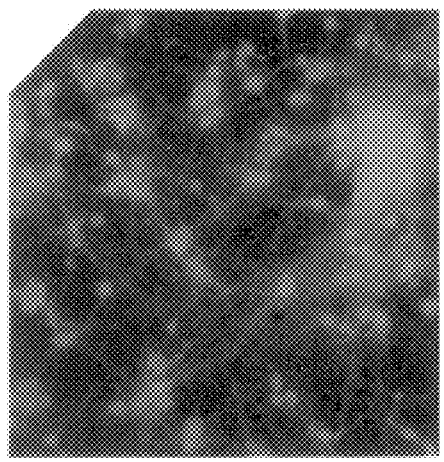
Figure 19D:
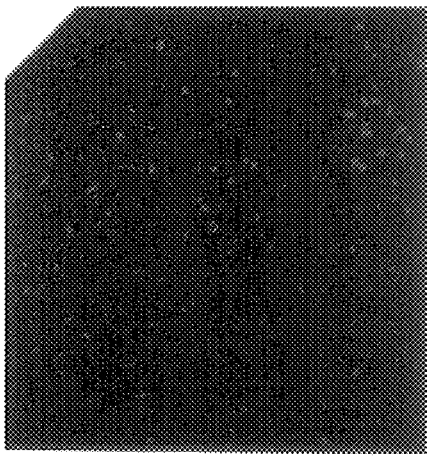
Figure 19E:
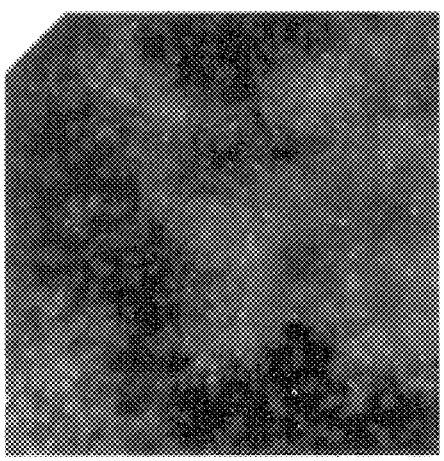
Figure 19F:
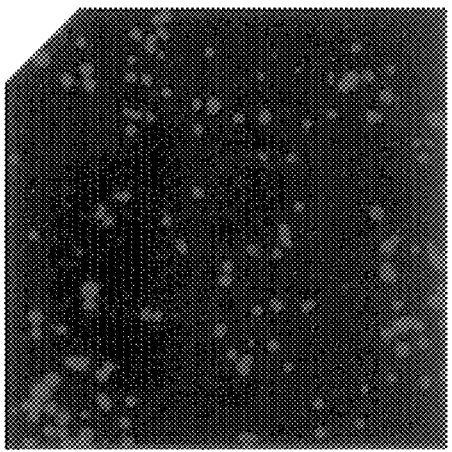
Figure 19G:
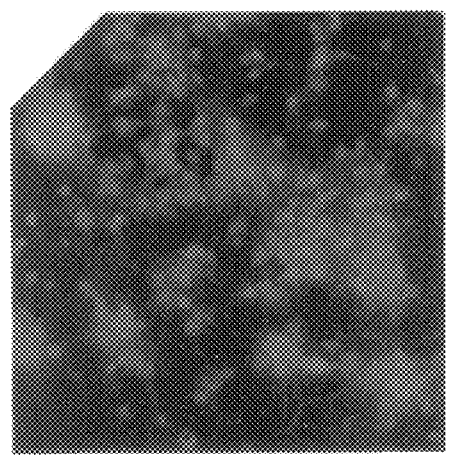
Figure 19H:
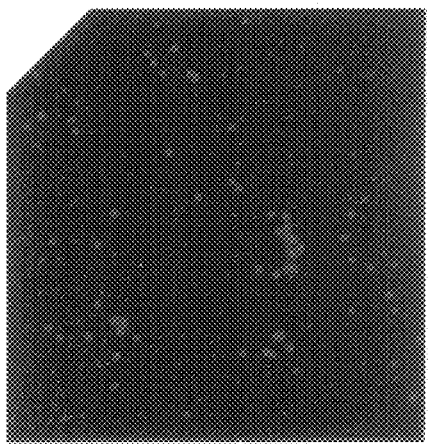
Figure 19I:
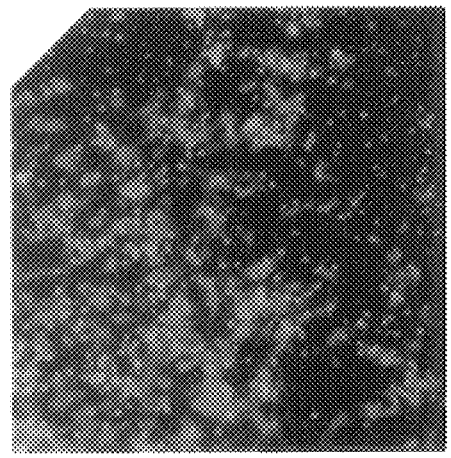
Figure 19J:
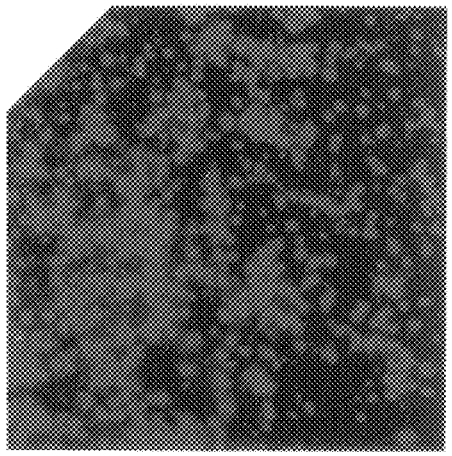
Figure 19K:
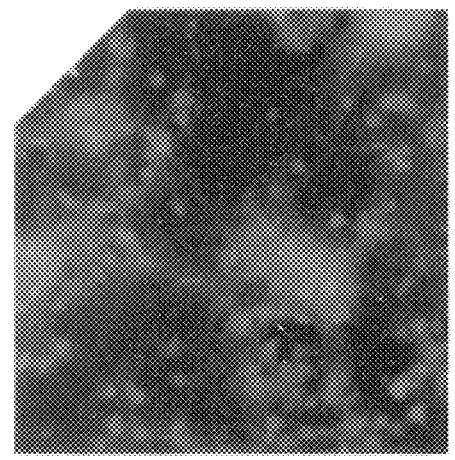
Figure 19L:
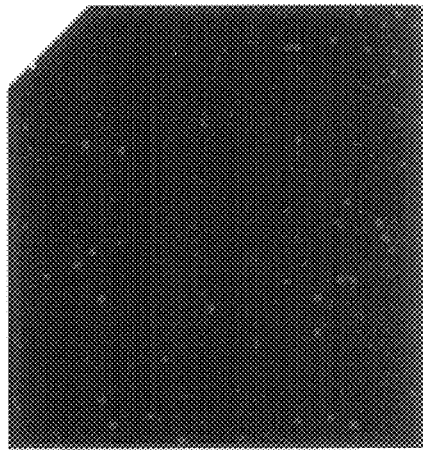

FIG. 18 shows the quantitative effect of AdlacZ versus Ad1101 infection on survival of cortical progenitor cells and postmitotic neurons, as measured using MTT assays. In FIG. 18A, cortical progenitor cells were infected with AdlacZ (black bars) or Ad1101 (grey bars) at 0, 10, 25, 50, or 100 MOI at the time of plating. Cell survival was assayed 3 days later using the MTT assay. A concentration dependent decrease in cell survival was detected in cells infected with Ad1101 relative to AdlacZ infected control cells. In FIG. 18B, at 8 days in vitro post-mitotic cortical neurons were infected at the same titres as described in FIG. 18A and the MTT assays carried out 4 days later. No change in cell survival was detected at any viral titre tested on neuronal cultures. Results represent the mean of three different experiments ± the standard error of the mean.

FIGS. 19A–L show a comparison of cell viability of cortical progenitors and neurons infected with recombinant AdlacZ and Ad1101 using Live/Dead staining. Cortical progenitors (two left columns) and cortical neurons (two right columns) were infected upon plating and at 8 days in vitro, respectively, with 25 MOI of AdlacZ (FIGS. 19E–H), Ad 1101 (FIGS. 19I–L), or were left uninfected (FIGS. 19A–D). Live cells were measured by the enzymatic conversion of permeant calcein-AM to fluorescent calcein (green). Dead cells were detected by the uptake of ethidium bromide into cell DNA (red). A dramatic increase in cell death accompanied by a drop in cell survival was detected in progenitor cells infected with AD1101 (FIGS. 19I, J) when compared to uninfected progenitor cells (FIGS. 19 A, B) or to those infected with AdlacZ (FIGS. 19 E ,F). In contrast, survival of cortical neurons was unaffected by infection with either AdlacZ (FIGS. 19 G, H) or Ad1101 (FIGS. 19 K, L) relative to uninfected neurons (FIGS. 19 C, D). Size bar for FIGS. 19A–L=50 μm.

Figure 20A:
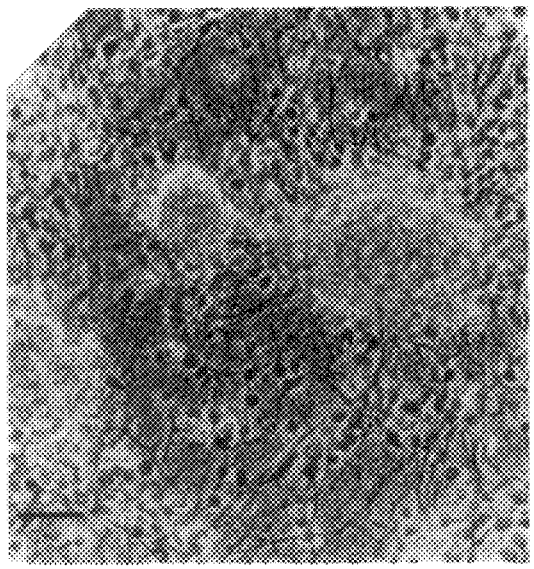
FIGS. 20(A–D) are photomicrographs showing 6 day old cultures of E 18 postmitotic cortical neurons. (A) Phase contrast micrograph of (B), and (B) anti-BrdU immunostaining after a 12 hour incubation with BrdU. (C) Phase contrast micrograph of (D) and (D) anti-MAP2 immunostaining.
Figure 20B:
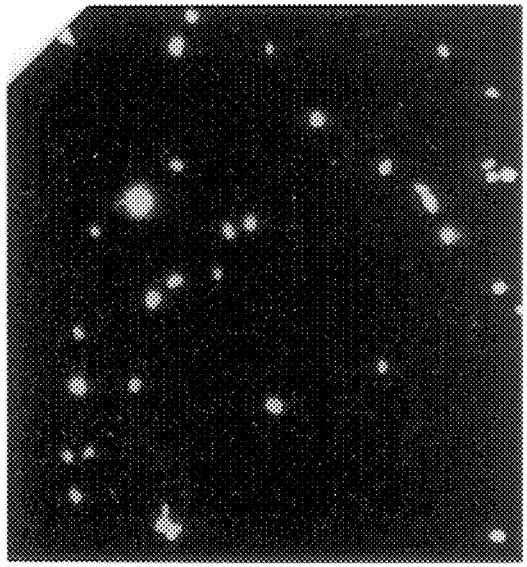
Figure 20C:
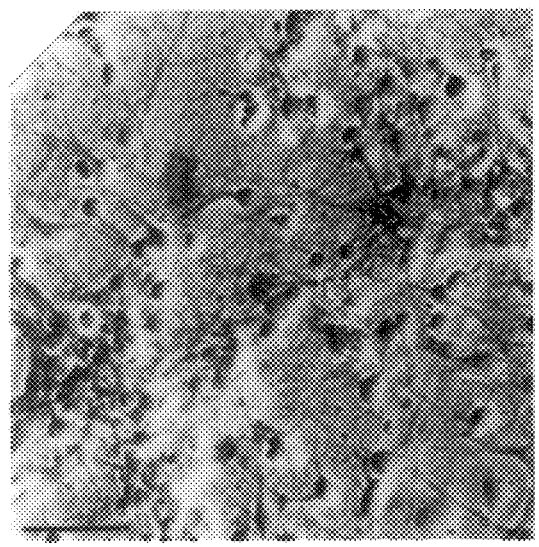
Figure 20D:
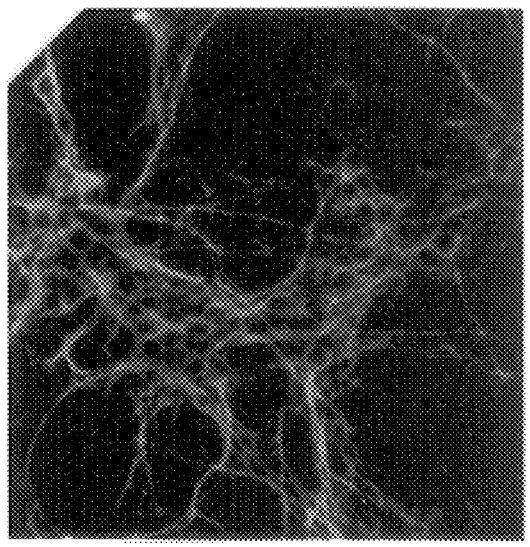
Figure 21A:
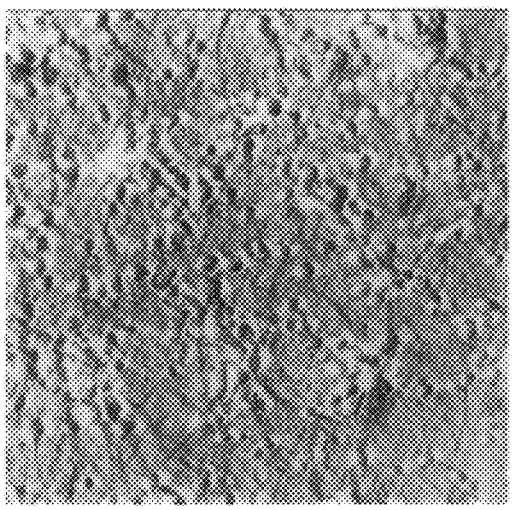
FIGS. 21(A–F) are photomicrographs showing that the survival of postmitotic cortical neurons is unaffected by functional ablation of pRb family members.
Figure 21B:
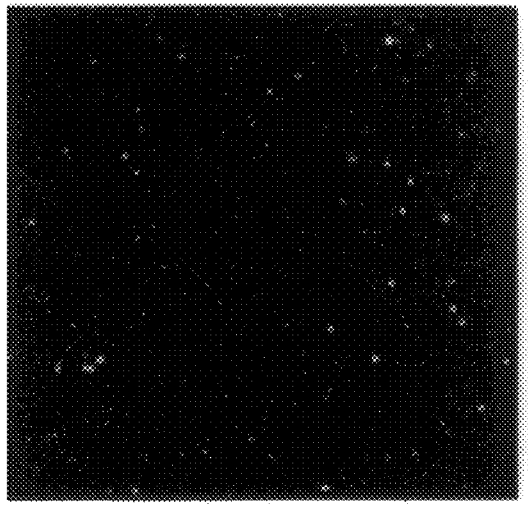
Figure 21C:
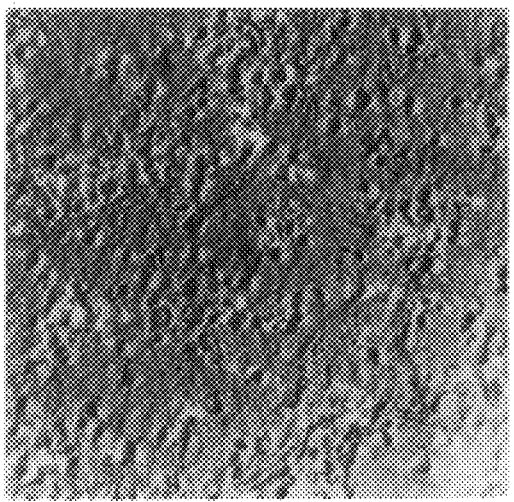
Figure 21D:
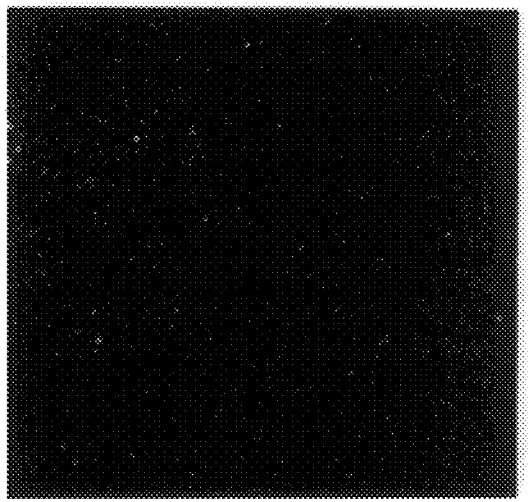
Figure 21E:
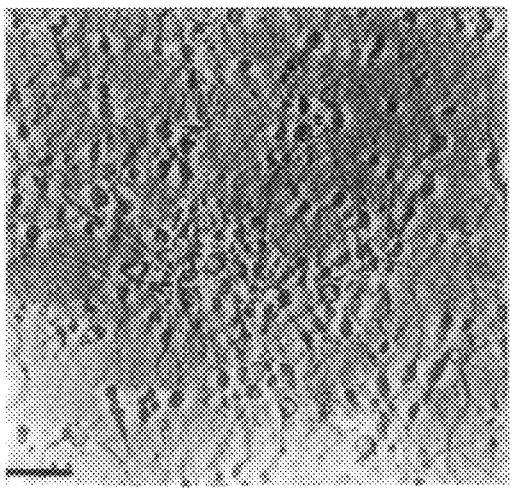
Figure 21F:
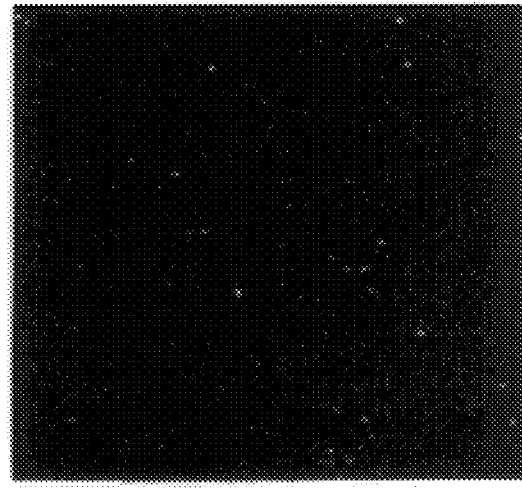

FIGS. 20A–D show a characterization of cultures of E18 postmitotic cortical neurons. After 6 days in culture the majority of cells in culture were postmitotic neurons, as indicated by the low level of anti-BrdU immunostaining after a 12 hour incubation with BrdU (FIG. 20B) relative to the total number of cells, as indicated by the phase contrast micrograph of the same field (FIG. 20A). The neuronal marker MAP2 was highly expressed at this stage as indicated by staining with anti-MAP2 (FIG. 20D). FIG. 20C shows a phase contrast micrograph of the same field. Scale bars: (FIGS. 20A, B) 50 μm; (FIGS. 20C, D) 50 μm.

FIGS. 21(A–F) show that the survival of postmitotic cortical neurons is unaffected by functional ablation of pRb family members. After 8 days in vitro cortical neurons were left uninfected (FIGS. 21A, B) or were infected with 25 MOI of AdlacZ (FIGS. 21C, D) or Ad 1101 (FIGS. 21E, F). Four days later, apoptosis was monitored by TUNEL-labeling. No increase in TUNEL positive cells was detected in neurons infected with Ad1101 (FIG. 21F) relative to AdlacZ (FIG. 21D) or to uninfected cells (FIG. 21B). FIGS. 21A, C, E) are phase contrast micrographs of fields of FIGS. 21B, D, F, respectively. Figures are representative of 6 separate experiments showing similar results. Scale bar for FIGS. 21A–F= 50 cm.

EXAMPLE X

ASSAYS FOR NEURONAL GROWTH

The experiments described below demonstrate methods for measuring the preferential growth response of sympathetic neurons to the neuronal growth factor NT-3, relative to growth in response to the neuronal growth factor BDNF. It is understood that analogous assays may be used to analyze the growth response of various types of neurons infected with recombinant adenoviruses, for example, an adenovirus encoding a neurotrophin receptor such as a Trk receptor.

NT-3 Selectively Promotes Neurite Extension in NGF-Dependent Sympathetic Neurons To determine whether sympathetic neurons responded to either NT-3 or BDNF after they become dependent upon target-derived NGF, we selected the NGF-dependent population of neonatal sympathetic neurons by culturing in 10 ng/ml NGF for 5 days (FIG. 22) and examined neurotrophin-mediated survival and neurite extension. To assay for survival responses, after selection in NGF, neurons were switched to 30 ng/ml NT-3 or BDNF. BDNF was not sufficient to support survival of NGF-dependent neurons; by 2 days after the switch, all of the neurons in the cultures were dead, as monitored by counting phase-bright cell bodies. In contrast, 25–30 ng/ml NT-3 was sufficient to support the survival of a small population of NGF-dependent neurons.

Figure 22A:
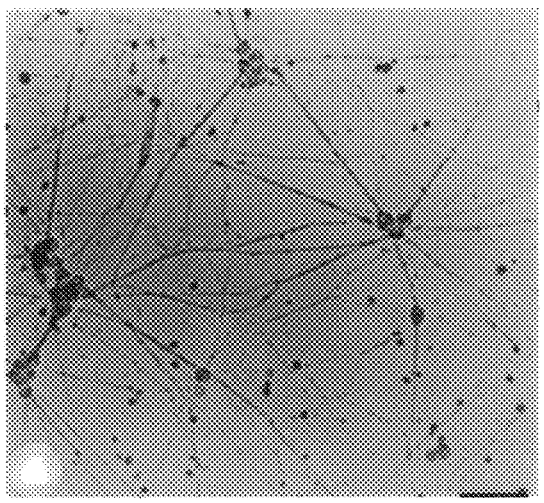
FIGS. 22(A–D) are photomicrographs showing that NGF-dependent sympathetic neurons growth-response to NT-3 but not to BDNF. Phase-contrast micrographs of cultures of pure sympathetic neurons from the postnatal day 1 rat SCG maintained in 10 ng/ml NGF for 5 days (A) and then supplemented with 30 ng/ml NT-3 (B) or 30 ng/ml BDNF (C). NT-3 enhanced the number of neurites compared with BDNF when examined 2 days after addition. In similar cultures where the NGF was replaced with ng/ml BDNF (D), obvious cell body and process deterioration was evident.
Figure 22B:
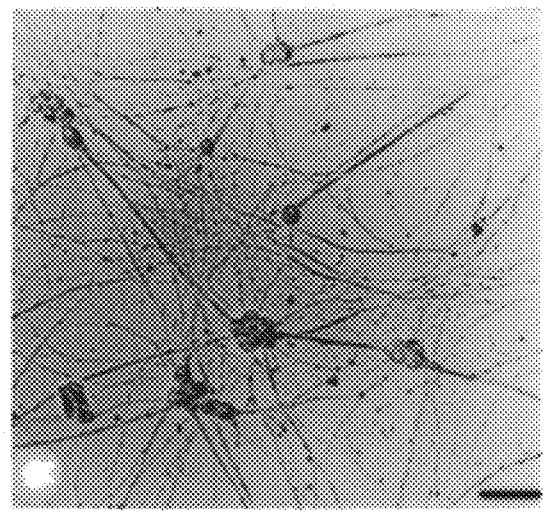
Figure 22C:
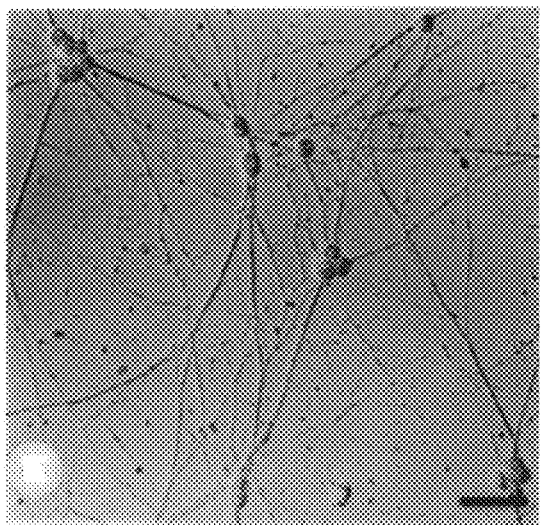
Figure 22D:
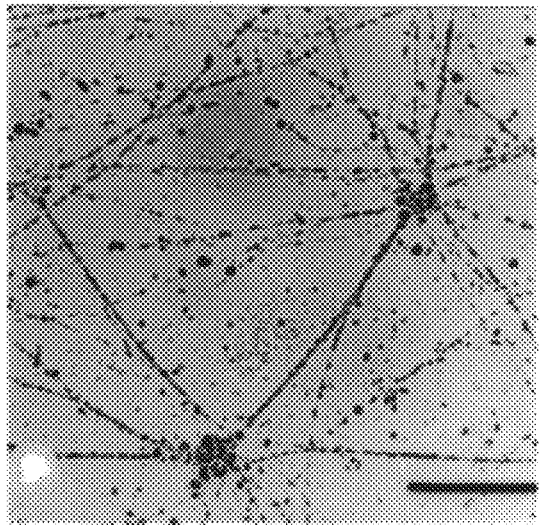
Figure 23A:
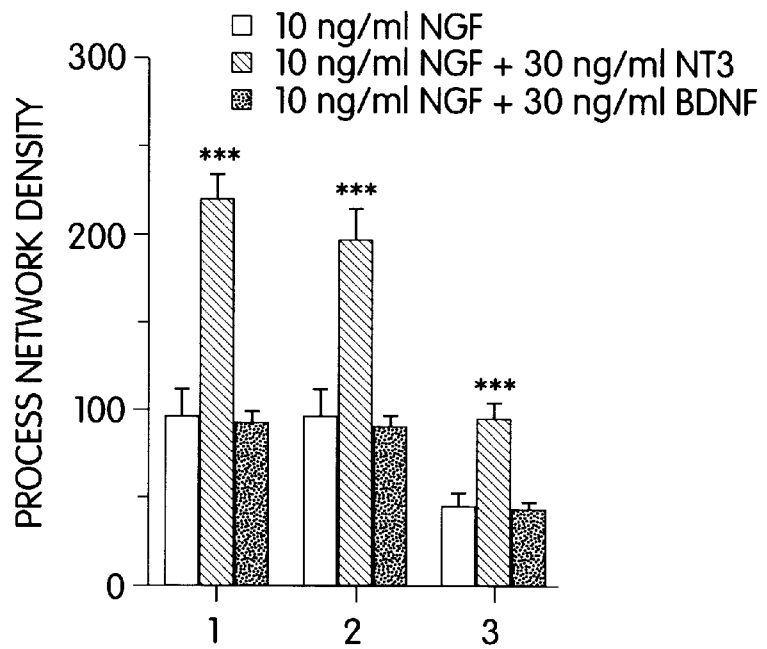
FIGS. 23(A–D) are graphs showing the process network density, total neurite length, and cell size of sympathetic neurons cultured in NGF alone, or NGF plus NT-3, as indicated on the X-axis.

To determine whether the addition of NT-3 or BDNF could mediate neurite extension independent of survival, sympathetic neurons were plated on collagen and selected in 10 ng/ml NGF for 5 days, and then 30 ng/ml NT-3 or BDNF was added in the presence of 10 ng/ml NGF for an additional 2 days. The addition of NT-3 led to a robust increase in the density of neuritic processes (FIG. 23A), with a 2- to 2.5-fold increase in neuritic density in each of three separate experiments. In contrast, addition of 30 ng/ml BDNF had no measurable effect (FIGS. 22C and 23A).

Figure 23B:
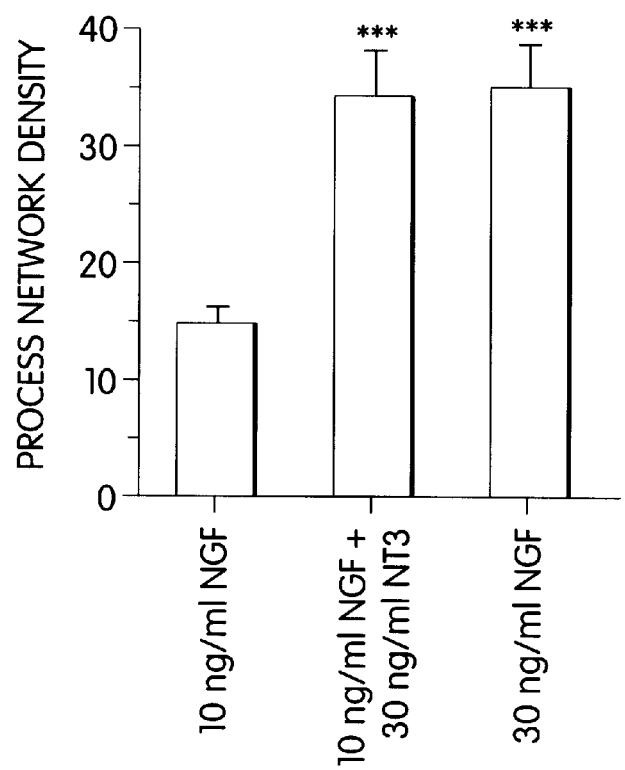
Figure 23C:
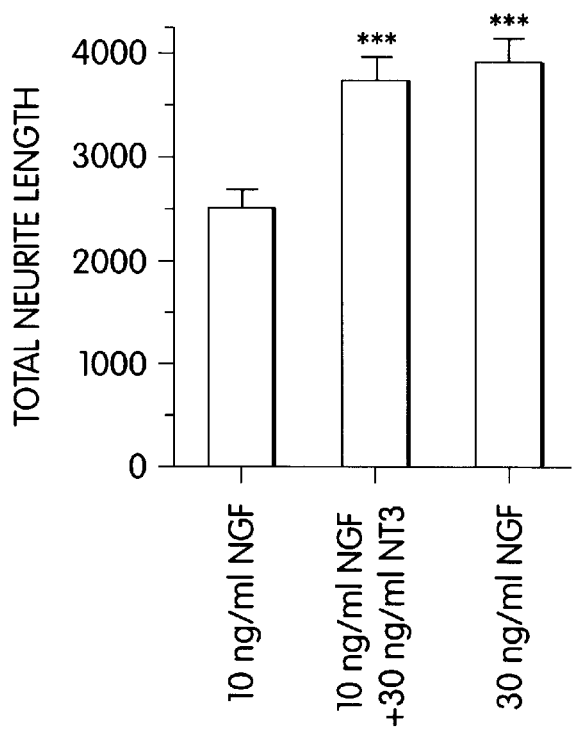
Figure 23D:
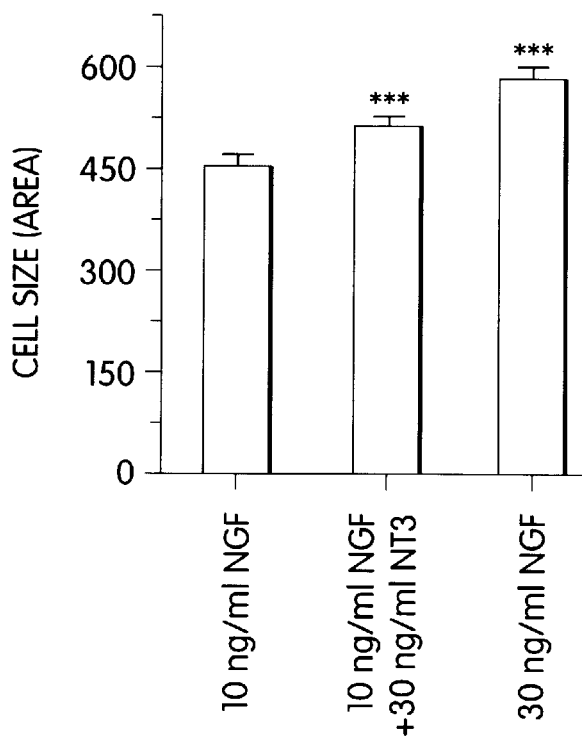

To more precisely define the effect of NT-3 on neuritogenesis, sympathetic neurons were plated at low density on poly-D-lysine/laminin, selected for 5 days in 10 ng/ml NGF, and then switched to 10 ng/ml NGF plus 30 ng/ml NT-3, or to 30 ng/ml NGF. Two days later, the process network density, total neurite length, and cell body size were all measured. As was seen in the higher density cultures (FIG. 23A), the process network density was increased 2- to 2.5-fold in the presence of 10 ng/ml NGF plus 30 ng/ml NT-3 (FIG. 23B). A statistically similar increase was noted with 30 ng/ml NGF. Similar results were obtained from measurements of total neurite length; both NT-3 and NGF mediated an ~1.5-fold increase (FIG. 23C). In contrast, NGF and NT-3 differentially regulated cell body size (FIG. 23D). Neurons cultured in 10 ng/ml NGF plus 30 ng/ml NT-3 displayed a small but significant (P=0.002) increase of 10%, whereas neurons cultured in 30 ng/ml NGF hypertrophied ~25–30%, an increase that was significantly greater than that obtained with NGF plus NT-3 (P<0.001). Thus, although NT-3 was approximately equivalent to NGF in its ability to promote neurite extension, it was significantly less effective in promoting cell body hypertrophy, and it was 20–40-fold less efficient at promoting neuronal survival.

NT-3 Selectively Induces Growth-Associated Gene Expression

In neonatal sympathetic neurons, NGF regulates the expression of the mRNAs encoding tyrosine hydroxylase, p75 neurotrophin receptor, and Tα1 α-tubulin in a graded, concentration-dependent fashion. To determine whether NT-3 regulates gene expression as it does neurite extension, sympathetic neurons were selected in 10 ng/ml NGF for 5 days, following which 10 or 30 ng/ml NT-3 was added in addition to 10 ng/ml NGF. RNA was isolated at time points ranging from 6–48 hours after addition. Northern blot analysis revealed that the addition of 30 ng/ml NT-3 for 6 hours led to a 5- to 10-fold increase in Tα1 α-tubulin mRNA, one member of the α-tubulin multigene family whose expression is regulated as a function of neuronal growth. This increase was maintained at 24 and 48 hours, consistent with the robust increase in neuritic process density induced by NT-3 addition, and was concentration-dependent: 10 ng/ml NT-3 elicited no significant increase in Tα1 α-tubulin mRNA. The magnitude of the increase observed with 30 ng/ml NT-3 was similar to that observed upon addition of 200 ng/ml NGF. Levels of Tα1 α-tubulin mRNA increase in a concentration-dependent fashion with increasing levels of NGF, with a plateau at 100–200 ng/ml. Thus, 30 ng/ml NT-3 was capable of eliciting as large an increase in Tα1 α-tubulin mRNA as saturating quantities of NGF. In contrast with NT-3, the addition of 30 ng/ml BDNF had no effect on expression of Tα1 α-tubulin mRNA.

The addition of 30 ng/ml NT-3 also led to a smaller, approximately two to three-fold increase in the expression of tyrosine hydroxylase mRNA. This increase, which was not elicited by 10 ng/ml NT-3, was first observed at 6 hours, and was subsequently maintained for 48 hours. Addition of BDNF had no effect on expression of tyrosine hydroxylase mRNA.

OTHER EMBODIMENTS

Figure 16:
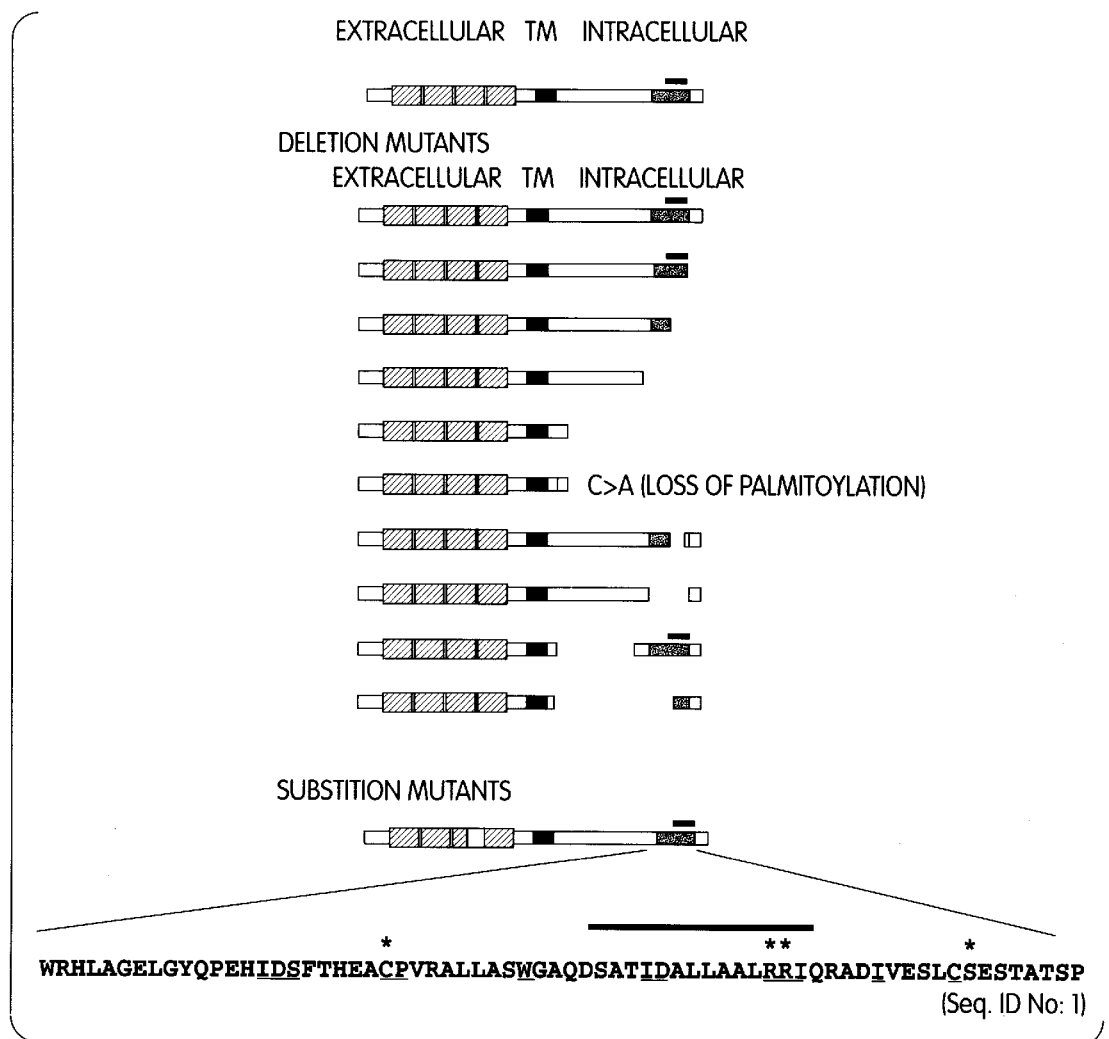
FIG. 16 is a schematic diagram illustrating wild-type p75 (uppermost illustration), deletion mutations, and substitution mutants. The region of homology with fas and TNFR1 is shown as a stippled bar in the intracellular domain (SEQ ID NO: 1). The potential G protein activating domain is shown as a solid bar. The substitution mutants are indicated by underlining.

The following groups of adenovirus constructs can be used according to the methods of the invention, as described herein: (1) wild-type p75, p75-truncation 1 (no DD), p75-truncation 2 (no ICD - to PvuII site), p75-truncation 2 (no ICD—to NarI site), p75 ICD, or p75 mICD; (2) pMAGE or other Mages; (3) Traf1, Traf2, Traf3, Tradd, Fadd/MORT-1, FP, FAP, or FAN; (4) IκB-α, IκB-β, Bcl-31, IκB-epsilon, or RelA/p65; (5) rhoA, rac1, cdc42, PAK1, PAK2, PAK3, GPAK, or Germinal centre (GC) kinase; (6) MEKK1, MEKK2, MEKK3, SEK1/MKK4, or Tpl-2; (7) SEK1, MKK3, MKK6, or MLK (mixed lineage kinases—SPRK, DLK, ZPK, MUK); (8) p54 JNK, p38 or MAPK; (9) jun, atf-2, Elk-1, or Max; (10) TrkA wild-type, TrkA Y490F (defective in Shc and PLC interactions), TrkA Y785F (defective in PLC interactions), TrkA Y490F/Y785F, TrkA KFG (dl441–443, defective in SNT interactions), TrkA K538A (kinase-inactive), or truncated TrkA (constitutively active with TM and ICD); (11) TrkA Y490F/Y785F/KFG (TrkAdef); (12) TrkA Y490F/KFG (specific for PLC interactions, or TrkA Y785F/KFG (specific for Shc interactions); (13) TrkAdef+ Pl-3K, TrkAdef+src, TrkAdef+ Grb2, TrkAdef+Syp, TrkAdef+rasGAP, or TrkAdef+STAT1; (14) all of the add-back mutants in combination with wild-type SNT (intact KFG), PLC (Y785), or Shc (Y490) sites; (15) the same series of unpublished and published mutants in the TrkB and TrkC genes; (16) Akt1, Akt2, Pl-3 kinase, or SHP; (17) c-yes, c-src, or c-fyn; (18) SOS, Gab1, Ras, rasGAP, B-raf, Raf-1, KSR, MEK1, MEK2, Rsk1, Rsk2, Rsk3, MAPK1, or MAPK2; (19) SH-PTP1, or SH-PTP2; (20) STAT1, STAT2, STAT3, STAT4, STAT5, STAT6, or PLC-γ1, PKCδ, PKCε, or PKCζ; (21) MPK1 or MPK2; (22) p53 or Csk; (23) JAK1, JAK2, JAK3, or GSK3; (24) bcl-2, bcl-x, bcl-xl, bax, or bak; and (25) wild-type p75 or the deletion or substitution mutants shown in FIG. 16.

What claimed is:

1. A method of generating a postmitotic neuron containing a purified recombinant adenovirus vector, wherein said vector comprises a DNA molecule encoding a non-adenoviral gene product that inhibits or induces apoptosis, said method comprising administering said adenovirus vector to a population of neurons at a multiplicity of infection of approximately 10 to approximately 50, the infection with said vector being sufficient to effect transduction of least 70% of said neurons.

2. The method of claim 1, wherein said protein encodes a protein that induces apoptosis.

3. The method of claim 1, wherein said neuron is a sympathetic neuron.

4. The method of claim 1, wherein said adenovirus vector further comprises a reporter gene.

5. The method of claim 4, wherein said reporter gene is selected from the group consisting of alkaline phosphatase, chloramphenicol acetyltransferase, lacZ, and green fluorescent protein.

6. The method of claim 1, wherein said DNA molecule encodes a tumor suppressor gene.

7. The method of claim 6, wherein said tumor suppressor gene is p53.

8. The method of claim 1, wherein said DNA molecule encodes a growth factor receptor.

9. The method of claim 8, wherein said growth factor receptor is Trk.

10. The method of claim 8, wherein said growth factor receptor is p75.

11. A method of inhibiting or inducing apoptosis in a postmitotic neuron, said method comprising infecting a population of neurons with a purified recombinant adenoviral vector, wherein said infecting is at a multiplicity of infection of approximately 10 to approximately 50, the infection with said vector being sufficient to effect transduction of least 70% of said neurons, said vector comprising DNA encoding a protein that inhibits or induces apoptosis.

12. The method of claim 1, wherein said protein is p53, or a biologically active fragment thereof.

13. The method of claim 11 or 1, wherein said MOI is 10.

14. The method of claim 11 or 1, wherein said MOI is 50.

15. The method of claim 1, wherein said DNA molecule encodes a protein that inhibits apoptosis.

16. The method of claim 15, wherein said protein is Bcl-xL.

17. The method of claim 15, wherein said protein is E1B55K.

18. The method of claim 15, wherein said protein is Gab1.

19. The method of claim 15, wherein said protein is Bcl-2.

20. A method of generating a postmitotic neuron containing a purified adenovirus vector, said method comprising:
   (a) infecting said postmitotic neuron with said adenovirus vector, and
   (b) expressing a gene product encoded by a DNA molecule contained within said vector, wherein said gene product is selected from Bcl-xL, E1B55K, and Gab1.

21. The method of claim 20, said neuron being infected while in tissue culture.

22. The method of claim 20, said neuron being infected in vivo.

23. The method of claim 20, wherein said neuron is a sympathetic neuron.

24. The method of claim 23, wherein said neuron is a dopaminergic neuron.

25. The method of claim 20, wherein said neuron is a cortical neuron.

26. A method of identifying a substance that induces apoptosis, said method comprising
   (a) culturing a population of postmitotic neurons;
   (b) infecting the neurons of said population with an adenovirus vector comprising DNA encoding a protein that inhibits apoptosis;
   (c) exposing a subset of the population of neurons infected in step (b) to a substance, said substance being suspected of inducing apoptosis; and
   (d) comparing the approximate number of neurons that undergo apoptosis in the subset of the population that was infected and exposed to said substance with the approximate number of neurons that undergo apoptosis in the population of cells that were infected, a relative increase in the number of apoptotic cells in the subset of the population indicating an effective inducer of apoptosis.

27. The method of claim 26, wherein said DNA encodes Bcl-2.

28. A method of identifying a substance that inhibits apoptosis, said method comprising
   (a) culturing a population of postmitotic neurons;
   (b) infecting the neurons of said population with an adenovirus vector comprising DNA encoding a protein that induces apoptosis;
   (c) exposing a subset of the population of neurons infected in step (b) to a substance, said substance being suspected of inhibiting apoptosis; and
   (d) comparing the approximate number of neurons that undergo apoptosis in the subset of the population that was infected and exposed to said substance with the approximate number of neurons that undergo apoptosis in the population of cells that were infected, a relative decrease in the number of apoptotic cells in the subset of the population indicating an effective inhibitor of apoptosis.

29. The method of claim 28, wherein said DNA encodes p53.

30. A method of identifying a substance that inhibits growth or proliferation, said method comprising
   (a) culturing a population of postmitotic neurons;
   (b) infecting the neurons of said population with an adenovirus vector comprising DNA encoding a protein that induces growth;
   (c) exposing a subset of the population of neurons infected in step (b) to a substance, said substance being suspected of inhibiting growth or proliferation; and
   (d) comparing the approximate number of neurons that undergo growth or proliferation in the subset of the population that was infected and exposed to said substance with the approximate number of neurons that undergo growth in the population of cells that were infected, a relative decrease in the expression of T$\alpha$1 $\alpha$-tubulin or a T$\alpha$1 $\alpha$-tubulin transgene indicating an effective inhibitor of growth or proliferation.

31. The method of claim 30, said protein being the TrkB receptor.

* * * * *